(12) United States Patent
Miyawaki et al.

(10) Patent No.: US 8,865,124 B2
(45) Date of Patent: Oct. 21, 2014

(54) PROBE REAGENT FOR MEASURING OXIDATIVE STRESS

(75) Inventors: Atsushi Miyawaki, Saitama (JP); Kazuki Sasaki, Tokyo (JP)

(73) Assignees: Japan Science and Technology Agency, Saitama (JP); Riken, Saitama (JP)

( * ) Notice: Subject to any disclaimer, the term of this patent is extended or adjusted under 35 U.S.C. 154(b) by 375 days.

(21) Appl. No.: 12/920,283

(22) PCT Filed: Feb. 27, 2009

(86) PCT No.: PCT/JP2009/054236
§ 371 (c)(1),
(2), (4) Date: Aug. 30, 2010

(87) PCT Pub. No.: WO2009/107876
PCT Pub. Date: Sep. 3, 2009

(65) Prior Publication Data
US 2011/0206615 A1  Aug. 25, 2011

(30) Foreign Application Priority Data

Feb. 29, 2008 (JP) ................................. 2008-049895

(51) Int. Cl.
| | | |
|---|---|---|
| A61K 51/00 | (2006.01) | |
| A61M 36/14 | (2006.01) | |
| G01N 33/50 | (2006.01) | |
| A61K 51/08 | (2006.01) | |
| A61K 49/14 | (2006.01) | |
| A61K 49/00 | (2006.01) | |
| C07K 14/00 | (2006.01) | |
| C12Q 1/28 | (2006.01) | |
| G01N 21/64 | (2006.01) | |
| G01N 33/84 | (2006.01) | |
| G01N 21/77 | (2006.01) | |

(52) U.S. Cl.
CPC ............ *G01N 33/5008* (2013.01); *A61K 51/08* (2013.01); *A61K 49/14* (2013.01); *A61K 49/0056* (2013.01); *A61K 49/0017* (2013.01); *A61K 51/088* (2013.01); *C07K 14/00* (2013.01); *C12Q 1/28* (2013.01); *G01N 21/6428* (2013.01); *G01N 21/77* (2013.01); *G01N 33/5014* (2013.01); *G01N 33/84* (2013.01); *G01N 2500/10* (2013.01)
USPC ......... 424/1.69; 424/1.11; 424/1.65; 424/9.1; 424/9.6

(58) Field of Classification Search
CPC ........... A61K 2123/00; A61K 2121/00; A61K 51/08; A61K 51/088; A61K 51/00; A61K 51/02; A61K 49/00; A61K 49/001; A61K 49/0013; A61K 49/0015; A61K 49/0017; A61K 49/0021; A61K 49/0056; A61K 49/12; A61K 49/14; A61K 38/00; A61K 38/02; A61K 38/16; G01N 33/5014; G01N 2500/10; G01N 33/5008; G01N 21/6428; G01N 21/77; G01N 33/84; C07K 14/00; C12Q 1/28
USPC ........... 424/1.11, 1.49, 1.65, 1.73, 1.81, 1.85, 424/1.89, 9.1, 9.6; 514/1, 1.1; 530/300, 530/326, 350, 402; 435/6.1, 69.1, 69.7, 435/69.8

See application file for complete search history.

(56) References Cited

U.S. PATENT DOCUMENTS

| | | | |
|---|---|---|---|
| 6,179,928 B1 * | 1/2001 | Carlton ............................. | 134/6 |
| 7,595,375 B2 * | 9/2009 | Miyawaki et al. ............. | 530/350 |
| 7,981,637 B2 * | 7/2011 | Miyawaki et al. ........... | 435/69.1 |
| 7,981,658 B2 * | 7/2011 | Miyawaki et al. ......... | 435/252.3 |
| 7,993,879 B2 * | 8/2011 | Tsien et al. .................. | 435/69.7 |
| 8,013,119 B2 * | 9/2011 | Nagai et al. ................... | 530/350 |
| 2003/0022198 A1 | 1/2003 | Kaelin, Jr. et al. | |
| 2006/0003961 A1 | 1/2006 | Semenza | |
| 2011/0206615 A1 | 8/2011 | Miyawaki et al. | |
| 2013/0298263 A1 | 11/2013 | Iwawaki et al. | |

FOREIGN PATENT DOCUMENTS

| | | |
|---|---|---|
| EP | 1 867 716 A1 | 12/2007 |
| JP | 2005-95171 | 4/2005 |
| WO | WO 2004/020458 A2 | 3/2004 |

OTHER PUBLICATIONS

Nagai et al, Nature Biotechnology, 2002, vol. 20, pp. 87-90.*
De Felipe, P. et al., "E unum pluribus: multiple proteins from a self-processing polyprotein", Trends in Biotechnology, Feb. 1, 2006, vol. 24, No. 2, Elsevier Publications, Cambridges, GB.

(Continued)

*Primary Examiner* — D L Jones
(74) *Attorney, Agent, or Firm* — Foley & Lardner LLP

(57) ABSTRACT

The present invention relates to fluorescent or luminescent probe reagents for measuring oxidative stress in a cell or an organism. Examples of the probe reagents include: a fluorescent or luminescent protein and a marker protein; a fluorescent or luminescent protein, a marker protein, and a regulatory factor; or a fluorescent or luminescent protein, a marker protein, a cleavage sequence, and a regulatory factor. In the probe reagents, the marker protein makes it possible to detect the oxidative stress caused by reactive oxygen species and comprises a regulatory factor-binding site and a ubiquitin-binding site; and the regulatory factor is a protein making it possible to regulate degradation of the marker protein in response to the reactive oxygen species. The present invention also relates to a method of measuring oxidative stress in a cell or an organism, or a method of screening a substance which suppresses or promotes the oxidative stress in a cell or an organism by using the probe reagent.

12 Claims, 9 Drawing Sheets

(56) References Cited

OTHER PUBLICATIONS

Bex, Claudia et al., "A yeast two-hybrid system reconstituting substrate recognition of the von Hippel-Lindau tumor suppressor protein", Nucleic Acids Research, Dec. 2007, vol. 35, No. 21, XP-002677873.
Zheng, Xiaowei et al., "Cell-type-specific regulation of degradation of hypoxia-inducible factor 1α: Role of subcellular compartmentalization", Molecular and Cellular Biology, Jun. 2006, p. 4628-4641, vol. 26, No. 12, , XP-002677874.
Li, Ying-Ping et al., "Hydrogen peroxide stimulates ubiquitin-conjugating activity and expression of genes for specific E2 and E3 proteins in skeletal muscle myotubes", American Journal of Physiology Cell Physiology, Oct. 2003, pp. C806-C812, vol. 285, No. 4 Part 1, XP002677875.
EP 09 71 4536.1 Supplementary Search Report, mailed Jul. 9, 2012.
International Search Report PCT/JP2009/054236 dated Apr. 28, 2009.
Wenge Li et al., "Nrf2 Possesses a Redox-sensitive Nuclear Exporting Signal in the Neh5 Transactivation Domain", Journal of Biological Chemistry, vol. 281, No. 37, 27251-27263.
Vsevolod V. Belousov et al., "Genetically encoded fluorescent indicator for intracellular hydrogen peroxide", Nature Methods, vol. 3, No. 4, Apr. 2006, p. 281-286.
Kristina Lindsten et al., "A transgenic mouse model of the ubiquitin/proteasome system", Nature Biotechnology, vol. 21, No. 8, Aug. 2003, pp. 897-902.
John S. Schneekloth et al., "Chemical Genetic Control of Protein Levels: Selective in Vivo Targeted Degradation", Journal of the Americal Chemical Society, 2004, 126 (12), 3748-3754.
Andrew Tsourkas et al., "Detection of Peroxidase/HO-Mediated Oxidation with Enhanced Yellow Fluorescent Protein", Analytical Chemistry, 2005, 77 (9), 2862-2867.
Yashihiro Miwa, "Visualizing Molecules in Living Mammalian Cells Using Degraton Probes", Seikagaku, 2006, p. 14-2, Abstract.
Harada, H. et al. "The combination of hypoxia-response enhancers and an oxygen-dependent proteolytic motif enables real-time imaging of absolute HIF-1 activity in tumor xenografts", Biochemical and Biophysical Research Communications, 2007, vol. 360, pp. 791-796.
Itoh, K. et al. "An Nrf2/Small Maf Heterodimer Mediates the Induction of Phase II Detoxifying Enzyme Genes through Antioxidant Response Elements", Biochemical and Biophysical Research Communications, 1997, vol. 236, pp. 313-322.
Itoh, K. et al. "Keap1 regulates both cytoplasmic-nuclear shuttling and degradation of Nrf2 in response to electrophiles", Genes to Cells, 2003, vol. 8, pp. 379-391.
Itoh, K. et al. "Keap1 represses nuclear activation of antioxidant responsive elements by Nrf2 through binding to the amino-terminal Neh2 domain", Genes Dev., 1999, vol. 13, pp. 76-86.
Johnson, D. et al. "Activation of the antioxidant response element in primary cortical neuronal cultures derived from transgenic reporter mice", Journal of Neurochemistry, 2002, vol. 81, pp. 1233-1241.
Johnson, J. et al. "The Nrf2-ARE Pathway: An Indicator and Modulator of Oxidative Stress in Neurodegeneration", Ann N Y Acad Sci., Dec. 2008, vol. 1147, pp. 61-69.
Katoh, Y., et al. "Evolutionary conserved N-terminal domain of Nrf2 is essential for the Keap1-mediated degradation of the protein by proteasome", Archives of Biochemistry and Biophysics, 2005, vol. 433, pp. 342-350.
Kobayashi A., et al. "Oxidative Stress Sensor Keap1 Functions as an Adaptor for Cul3-Based E3 Ligase to Regulate Proteasomal Degradation of Nrf2", Molecular and Cellular Biology, Aug. 2004, vol. 24, No. 16, pp. 7130-7139.
Motohashi, H. et al. "Nrf2-Keap1 defines a physiologically important stress response mechanism", Trends in Molecular Medicine, Nov. 2004, vol. 10, No. 11, pp. 549-557.
Rushmore, T. et al. "The Antioxidant Responsive Element", The Journal of Biological Chemistry, vol. 266, No. 18, Issue of Jun. 25, 1991, pp. 11632-11639.

* cited by examiner

Fig. 6

EtOH    DEM            DMSO    MG132

*                    *

PROBE REAGENT FOR MEASURING OXIDATIVE STRESS

CROSS-REFERENCE TO RELATED APPLICATIONS

This application is the U.S. national phase of PCT/JP2009/054236 filed Feb. 27, 2009; which claims priority from Japanese Application No. 2008-049895 dated Feb. 29, 2008. The subject matter of each of the above-referenced applications is incorporated in entirety by reference.

SEQUENCE LISTING

The instant application contains a Sequence Listing which has been submitted in ASCII format via EFS-Web and is hereby incorporated by reference in its entirety. Said ASCII copy, created on Nov. 19, 2010, is named 81356362.txt and is 6,237 bytes in size.

TECHNICAL FIELD

The present invention relates to fluorescent or luminescent probe reagents for measuring oxidative stress in a cell or an organism.

The present invention also relates to nucleic acids encoding the probe reagents, and vectors comprising the nucleic acids.

The invention further relates to a method of measuring oxidative stress or a method of screening an oxidative stress-regulating substance in a cell or an organism by using the probe reagent or vector.

The present invention further relates to a kit for measuring oxidative stress or screening an oxidative stress-regulating substance, comprising the probe reagent, nucleic acid, or vector.

BACKGROUND ART

Recently, an excessive oxidation reaction, what is called oxidative stress, occurring inside cells has been found to exert harmful effects in living bodies. This oxidation reaction is evoked by a molecular, what is called "reactive oxygen species (ROS)" which has a strong oxidative power generated inside cells. Examples of the known ROS include hydrogen peroxide, singlet oxygen, hydroxyl radical, superoxide anion, and the like. In nature, the ROS is used for elimination of a foreign substance in the immune system, detoxification of harmful molecules, or the like, and it also has useful aspects in vivo. In addition, there exists a system of eliminating the ROS by an enzyme or a molecule having an antioxidative capability in cells. Thus, the harmful effects of the ROS are inhibited by rapid removal of excessively generated ROS.

However, when a balance between the generation and the elimination of the ROS is lost so that the generation of the ROS becomes excessive, it initiates to exert the harmful effects in vivo. The oxidative stress damages molecules (such as DNA, protein, or lipid) that are essential for normal activities of cells. As a result, ageing and diseases such as cancer, arteriosclerosis, myocardial infarction, and diabetes can probably be caused. The oxidative stresses induced by unhealthy lifestyle such as excessive exercises, inadequate exercises, unbalanced diet, and smoking. The oxidative stress has become an issue closely related to current life.

Additionally, ROS has been a focus of attention as the pathogenesis of ischemia-reperfusion injury. In ischemia, the organs where the blood flow stopped are placed in the absence of oxygen, and a large amount of the ROS is generated by rapid reoxygenation after the reperfusion. This phenomenon damages a wide range of cells, and probably evokes an injury at an organ level. A risk causing the reperfusion injury makes prompt treatment difficult in the ischemic organs (Droge, W., Physiol. Rev., 82, 47-95, 2002).

Thus, under the situation in which various disadvantageous effects by ROS are discussed, measuring changes in distribution and amount of ROS generated in vivo should give an important insight in respect to a mechanism of disease development and ageing, and should further contribute largely to the development of the effective prophylaxis and treatment. For this purpose, a technique to efficiently measure the behavior of ROS in vivo is required.

An Example of a method of measuring ROS include a method using a chemiluminescent reagent such as isoluminol. This method is to measure a luminescent signal that is accompanied with an oxidation reaction of the reagent with the ROS. This reaction is widely used as a method of evaluating an immunological activity of leukocytes in order to measure ROS released during the attack against a foreign substance that enters a living body (Dahlgren, C. and Karlsson, A., J. Immunol. Meth., 232, 3-14, 1999). Unfortunately, isoluminol has a poor permeability across cell membranes. So, the measurement of ROS released outside cells can be performed, but the method is unsuitable for the measurement of ROS generated inside the cells. In addition, the intensity of this luminescence is weak. Since the method requires a large number of cells for this measurement and a prolonged integration time even for a high-sensitive detector, it is difficult to efficiently measure the ROS.

A measurement using an organic fluorescent dye has been also carried out. The dye, 2',7'-dichlorodihydrofluorescein, dihydroethidium, and the like are widely used (Munzel, T., et al., Arterioscler. Thromb. Vasc. Biol., 22, 1761-1768, 2002). Although these are nonfluorescent compounds under non-oxidative condition, these compounds become fluorescent by changing their structures due to an oxidation reaction with ROS. This fluorescent intensity indicates to an amount of the ROS in situ. These reagents can be introduced in cells by passing through cell membranes. However, since these reagents cannot be selectively localized in a particular organelle inside the cells, it is difficult to measure the ROS at a particularly localized area. Moreover, the fluorescence emission of these dyes is irreversible, and these cannot repeat the measurement because once the oxidized dye lose the reactivity with the ROS any more.

Recently, a fluorescent protein has been isolated from *Aequorea victoria*. One improved in its feature is widely used as a probe reagent for measuring a physiological activity in cells. A probe reagent that is composed of proteins can be used as a form of the gene. By being incorporated into cells as a plasmid, the expressed probe reagent can be used for the measurement. This method also allows only a specific cell in a living body or a specific organelle in cells to limitedly express the probe reagent, and makes it possible to measure the physiological activity at a more limited region.

There have been developed oxidative stress probe reagents using fluorescent proteins. Such reagents have a structure in which the fluorescent protein is fused to a marker protein that detects ROS. A protein that changes its structure due to the reaction with the ROS is used as the marker protein. The change in the structure is designed to change the intensity and wavelength of the fluorescence emitted by the fluorescent protein. For example, a probe reagent, what is called "Hyper", uses a protein reacting specifically with hydrogen peroxide as a sensor protein, and the protein has a structure attached to a fluorescent protein, YFP. The reaction of hydrogen peroxide with the sensor protein results in change in fluorescent intensity of YFP (Belousov, V. V., et al., Nature Methods, 3, 281-286, 2006 Rev., 82, 47-95, 2002). Another example includes an application using fluorescence resonance energy transfer. This probe reagent has a structure in which a sensor protein is sandwiched between two types of fluorescent proteins having different fluorescent wavelength. The change in the structure resulting from the reaction of the sensor protein with the ROS alters the distance between the fluorescent proteins at each end. This change in distance gives a change in the efficiency of the energy transfer. This reagent can monitor ROS by measuring a change in fluorescence spectra (JP Patent Publication (Kokai) No. 2005-95171A). However, the fluorescent change that is based on the structural change of the sensor protein of the reagent is small, and the detection becomes difficult when ROS is slightly produced in particular.

There is a protein that is expressed for a protective response against oxidative stress when cells are exposed to the stress. The oxidative stress of the cells can be detected by measuring an increase in expression of such a protein. In an example that has measured oxidative stress in muscle, proteins such as TNFα and pIκB have been measured as indicators of the oxidative stress (JP Patent Publication (Kokai) No. 2006-162346A). In this method, the intended proteins are measured using a biochemical technique such as Western blotting. Specifically, proteins in cells are extracted by disrupting the cells and then the proteins are subjected to separation. Thus, because the troublesome procedures are required in the prior art, it is impossible to measure the ROS quickly and continuously in living cells

DISCLOSURE OF THE INVENTION

As described in Background Art, under the situation in which various disadvantageous effects by ROS are discussed, precisely measuring a change in distribution and amount of ROS generated in living bodies is expected to give an important insight in respect to a mechanism of disease and ageing in which the ROS is involved, and to further contribute largely to the development of the effective prophylaxis and treatment. However, the above-mentioned problems have been pointed out in currently used or proposed methods of measuring ROS that evoke oxidative stress. Hence, there are demands for techniques that can efficiently measure behavior of ROS in vivo to overcome these problems.

Accordingly, it is an object of the present invention to provide fluorescent or luminescent probe reagents that are reversible for a response to ROS, thereby enabling monitoring oxidative stress continuously and in real-time in a cell or an organism.

It is another object of the present invention to provide methods of measuring oxidative stress in a cell or an organism, or a method of screening a substance which inhibits or promotes oxidative stress in a cell or an organism, by using the above probe reagent or vector comprising the DNA encoding the reagent.

It is still another object of the present invention to provide a kit for measuring an oxidative stress-related event, wherein the kit comprises the probe reagent, DNA or RNA, or vector.

To solve the above problems, the present inventors have now developed a new fluorescent probe reagent that can monitor the kinetics of the oxidative stress in living cells. This probe reagent comprises a fusion protein comprising 2 to 4 elements, i.e. at least a fluorescent or luminescent protein and a marker protein, and optionally further comprising a regulatory sequence and a cleavage sequence. Introducing a nucleic acid (i.e., DNA or RNA) encoding the probe reagent into cells so as to express it in the cells enables monitoring an increase or decrease of oxidative stress based on changes in fluorescent or luminescent intensity of the fluorescent or luminescent protein. Since an amount of the probe reagent changes dynamically in response to changes in oxidative stress, a big change in the fluorescent intensity can be obtained by utilizing an intrinsic reaction that degrades proteins in the cell. The feature of the probe that makes a continuous monitoring possible is based on the fact that the response to ROS is reversible.

In summary, the present invention includes the following features.

(1) A fluorescent or luminescent probe reagent for measuring oxidative stress in a cell or an organism, the reagent being constituted of a fusion protein comprising:
a fluorescent or luminescent protein;
a marker protein;
a cleavage sequence; and
a regulatory factor,
wherein
the marker protein makes it possible to detect the oxidative stress caused by ROS, and comprises a regulatory factor-binding site and a ubiquitin-binding site;
the regulatory factor is a protein capable of regulating degradation of the marker protein in response to the ROS;
the fluorescent or luminescent protein and the marker protein are adjacent to each other in any order so as to form a fusion molecule;
the cleavage sequence is positioned between the fusion molecule and the regulatory factor, and comprises a cleavable sequence;
the reagent is cleaved at the cleavage sequence in the cell or the organism, so that the fusion molecule and the regulatory factor are present separately; and
binding or dissociation between the regulatory factor and the marker protein promotes or inhibits the degradation of the marker protein.

(2) The probe reagent of (1) above, wherein the elements of the fusion protein are positioned from N-terminus to C-terminus in the following order:
(i) the fluorescent or luminescent protein, the marker protein, the cleavage sequence, and the regulatory factor;
(ii) the marker protein, the fluorescent or luminescent protein, the cleavage sequence, and the regulatory factor;
(iii) the regulatory factor, the cleavage sequence, the fluorescent or luminescent protein, and the marker protein; or
(iv) the regulatory factor, the cleavage sequence, the marker protein, and the fluorescent or luminescent protein.

(3) The probe reagent of (1) or (2) above, wherein the fluorescent or luminescent protein is degraded so as not to emit fluorescence or luminescence when the marker protein is degraded.

(4) The probe reagent of any of (1) to (3) above, wherein structural change of the regulatory factor in response to the ROS is reversible.

(5) The probe reagent of any of (1) to (4) above, wherein the degradation of the marker protein is caused by proteasome.

(6) The probe reagent of any of (1) to (5) above, wherein the oxidative stress is measurable in real-time.

(7) The probe reagent of any of (1) to (6) above, further comprising a linker between the fluorescent or luminescent protein and the marker protein.

(8) The probe reagent of any of (1) to (7) above, wherein the fluorescent or luminescent protein is a fluorescent protein derived from coral or Aequorea victoria.

(9) The probe reagent any of (1) to (7) above, wherein the fluorescent or luminescent protein is luciferase.

(10) The probe reagent of any of (1) to (9) above, wherein the marker protein and the regulatory factor are human Nrf2 (Accession No. AAB32188) and human Keap1 (Accession No. AAH21957) respectively, or are a homolog or analog thereof.

(11) The probe reagent of any of (1) to (10) above, wherein the probe reagent is encoded by a DNA comprising the nucleotide sequence shown in SEQ ID NO: 7.

(12) A DNA or RNA encoding the probe reagent of any of (1) to (11) above.

(13) The DNA of (12) above, wherein the DNA comprises the nucleotide sequence shown in SEQ ID NO: 7.

(14) A vector comprising the DNA of (12) or (13) above.

(15) The vector of (14) above, further comprising a regulatory sequence allowing the DNA to express.

(16) A method of measuring oxidative stress in a cell, the method comprising:
introducing the probe reagent of any of (1) to (11) above or the vector of (14) or (15) above into a cell or an organism excluding human; and
measuring the oxidative stress based on a fluorescent or luminescent intensity in the cell or the organism.

(17) The method of (16) above, wherein the measurement is performed in real-time.

(18) A method of measuring oxidative stress in a cell or an organism excluding human, the method comprising the steps of:
introducing the fusion molecule or a vector comprising a nucleic acid encoding the fusion molecule in the cell or the organism, thereby localizing the fusion molecule in the cell or the organism, wherein the fusion molecule comprises a fluorescent or luminescent protein and a marker protein whose degradation is regulated depending on degrees of the oxidative stress in the cell or the organism; and
measuring an amount of fluorescent or luminescent derived from the fluorescent or luminescent protein to determine the presence of a level of the oxidative stress in the cell or the organism based on a degree of regulation of degradation of the fusion molecule, wherein the marker protein comprises a regulatory factor-binding site and a ubiquitin-binding site, and the degradation of the fusion molecule is regulated by a regulatory factor in response to ROS.

(20) The method of (18) or (19) above, wherein the regulatory factor is either exogenous or endogenous.

(21) The method of any of (18) to (20) above, wherein the exogenous regulatory factor is introduced into the cell or the organism in the form of a vector comprising a DNA encoding the regulatory factor.

(22) A fluorescent or luminescent probe reagent for measuring oxidative stress in a cell or an organism, the reagent comprising a fusion molecule comprising a marker protein and a fluorescent or luminescent protein, wherein the marker protein comprises a regulatory factor-binding site and a ubiquitin-binding site and makes it possible to detect the oxidative stress caused by ROS, wherein the regulatory factor is a protein making it possible to regulate degradation of the marker protein in response to the ROS, and wherein the degradation of the marker protein is promoted or inhibited through binding or dissociation between the regulatory factor and the marker protein.

(23) A DNA or RNA encoding the probe reagent of (22) above.

(24) A vector comprising the DNA of (23) above.

(25) A fluorescent or luminescent probe reagent for measuring oxidative stress in a cell or an organism, the reagent comprising a fusion molecule, which comprises a marker protein and a fluorescent or luminescent protein, and a regulatory factor, wherein the regulatory factor is fused to the fusion molecule via a linker, wherein the marker protein comprises a regulatory factor-binding site and a ubiquitin-binding site and makes it possible to detect the oxidative stress caused by ROS, wherein the regulatory factor is a protein making it possible to regulate degradation of the marker protein in response to the ROS, and wherein the degradation of the marker protein is promoted or inhibited through binding or dissociation between the regulatory factor and the marker protein.

(26) A method of screening for an oxidative stress-regulating substance, the method comprising:
introducing a candidate substance and the probe reagent of any of (1) to (11), (22) and (25) above or the vector of (14), (15) or (24) above, into a cell or organism (excluding human), which has been loaded with oxidative stress; and
screening for the substance which decreases or increases a fluorescent or luminescent intensity in the cell or organism.

(27) A kit for measuring oxidative stress or screening an oxidative stress-regulating substance, the kit comprising at least one member selected from the group consisting of the probe reagents of any of (1) to (11), (229 and (25) above, the DNAs or RNAs of (12), (13) or (23) above, and the vectors of (14), (15) or (24) above.

The present application includes the contents of the specification and/or drawings of JP Patent Application No. 2008-049895 to which the present application claims the priority.

BRIEF DESCRIPTION OF THE DRAWINGS

FIG. 6 shows a result of Western blotting using an anti-Nrf2 antibody 8 hours after DEM, EtOH, MG132 or DMSO was added at a concentration of 100 μM, 0.1%, 10 μM, or 0.1%, respectively, to a cell that the fluorescent oxidative stress probe of the present invention has been introduced into. The symbol "*" denotes mKO2-Nrf2, and the symbol "**" denotes mKO2-Nrf2-T2A-Keap1 which is not separated at T2A.

BEST MODE FOR CARRYING OUT THE INVENTION

The present invention is further described in detail.

1. New Probe Reagent

As described above, the present inventors have now developed a probe reagent (which may simply be referred to as "probe") that overcomes the above-mentioned problems with prior art methods of measuring oxidative stress. This reagent consists essentially of proteins. Thus, the reagent can be expressed and function in a cell or an organism by introducing a nucleic acid (e.g., a gene, a DNA, an RNA, or a chemically modified molecule thereof) encoding the proteins into the cell or the organism. The part of the structure includes a fluorescent or luminescent protein, and a marker protein which detects oxidative stress. The increase or decrease of the oxidative stress is monitored by measuring a change in the fluorescent or luminescent intensity of the fluorescent or luminescent protein. Since an existing amount of the probe reagent changes dynamically in response to changes in oxidative stress, a big change in the fluorescent or luminescent intensity can be obtained by utilization of an intrinsic reaction that degrades proteins in the cell. In addition, the response is reversible, and the increase or decrease of the oxidative stress can be monitored continuously in a living cell or an organism. The features of this probe reagent are described below. In the present invention, there are provided the following related probe reagents.

A first probe reagent includes a fusion molecule comprising a marker protein and a fluorescent or luminescent protein. Introduction of this fusion molecule into a cell or an organism (in this case, a vector that contains a nucleic acid encoding the fusion molecule may be introduced into a cell or an organism) makes it possible to measure the presence of or a level (or a degree) of oxidative stress caused by ROS. This is mediated by the interaction between the fusion molecule and a endogenous regulatory factor that regulates degradation of a marker protein in response to the ROS.

A second probe reagent of the present invention is a fusion protein comprising a fluorescent or luminescent protein that emits fluorescence or luminescence, a marker protein, a regulatory factor regulating degradation of the marker protein in response to ROS, and a cleavage sequence, in which these elements are ligated to be a single amino acid chain. The structure is shown in FIG. 1.

Figure 1:
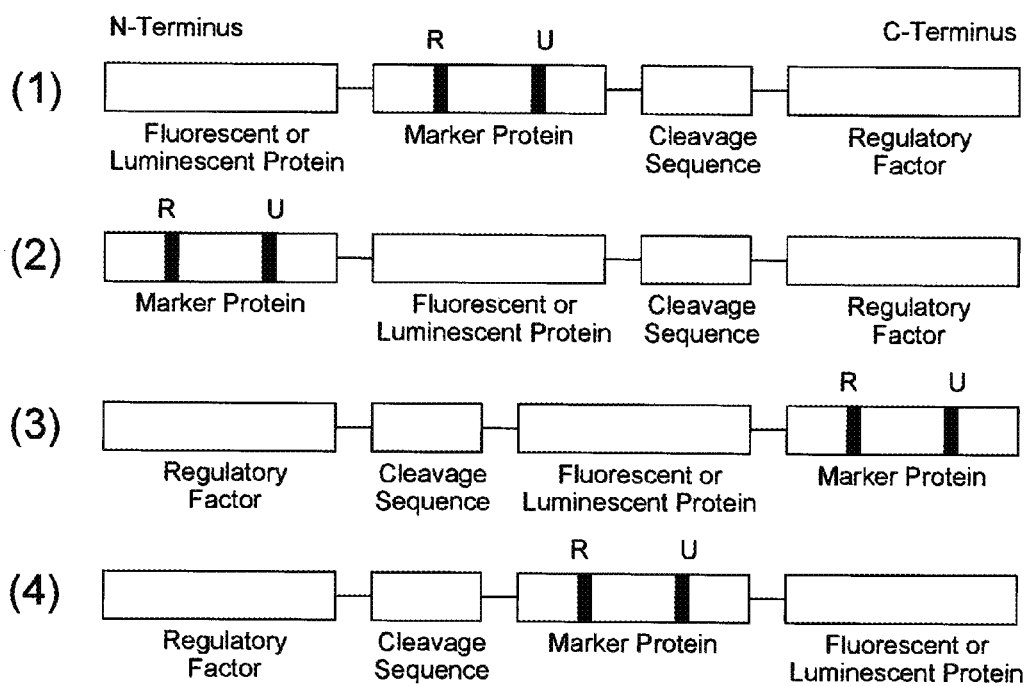
FIG. 1 depicts four possible structures of the fluorescent oxidative stress probe reagent of the present invention. Symbols "R" and "U" within a marker protein represent a regulatory factor-binding site and a ubiquitin-binding site, respectively.

As shown in FIG. 1, the probe reagent of the present invention can include four possible structures, wherein the elements are positioned in the following order from N-terminus to C-terminus: (1) the fluorescent or luminescent protein, the marker protein, the cleavage sequence, and the regulatory factor, (2) the marker protein, the fluorescent or luminescent protein, the cleavage sequence, and the regulatory factor, (3) the regulatory factor, the cleavage sequence, the fluorescent or luminescent protein, and the marker protein, or (4) the regulatory factor, the cleavage sequence, the marker protein, and the fluorescent or luminescent protein.

A third probe reagent is a probe comprising the above fusion molecule and the regulatory factor, in which these are linked via a linker. The linker should have an enough length to allow the regulatory factor to bind to a regulatory factor-binding site on the marker protein that constitutes the fusion molecule. Examples of the linker include, for example, a peptide or polypeptide linker that is composed of natural amino acids, non-natural amino acids or mixtures thereof. Specifically, a linker composed of approximately 18 amino acids or even a linker composed of approximately 142 amino acids can achieve the above advantageous effects of the present invention.

In the probe reagent of the present invention, a fluorescent or luminescent protein is linked adjacently to a marker protein. Either sequence of the proteins may position at the N-terminal side or the C-terminal side. A linker (e.g., a linker composed of one or several amino acids, such as a peptide composed of 10 or less amino acids) may be contained between the fluorescent or luminescent protein and the marker protein. The marker protein has a binding site for a regulatory factor and a site that binds to a protein molecule, which is called ubiquitin that is localized in cells and is involved in degradation of proteins.

The cleavage sequence is positioned between the regulatory factor and the fusion molecule of fluorescent or luminescent protein-marker protein. Either the regulatory factor or the fusion molecule that is the fluorescent or luminescent protein-marker protein may position at the N-terminal side or the C-terminal side, and the cleavage sequence is sandwiched between the regulatory factor and the fusion molecule.

The probe reagent of the present invention may be introduced directly into a cell in the form of a protein, or may be expressed and translated by introducing into a cell a vector that contains a DNA encoding the probe reagent. Among the probe reagents, the second probe reagent is automatically cleaved at the cleavage sequence in the cell (during the translation), and the regulatory factor is separated from the fusion molecule that is the fluorescent or luminescent protein-marker protein. In accordance with the present invention, the regulatory factor changes its structure due to a reaction with ROS so that the binding to or dissociation from the marker protein promotes or inhibits degradation of the marker protein. Thus, this enables the qualitative or quantitative measurement of oxidative stress.

The fluorescent or luminescent protein and the marker protein constitute the fusion molecule in which the fluorescent or luminescent protein is also preferably degraded and fails to emit fluorescence or luminescence when the marker protein is degraded.

The response of the probe reagent to oxidative stress can be made reversible by selecting, as the regulatory factor, a molecule in which the structural changes caused by a reaction with ROS are reversible. In order to exhibit a change of oxidative stress as a larger change in fluorescence or luminescence, the regulatory factor used is desirable to be a molecule that strongly promotes or inhibits degradation of the marker protein to the extent of oxidative stress that a cell receives in vivo.

Oxidative stress means a phenomenon that an excessive oxidation reaction inside a cell (i.e., a condition in which a balance between oxidation and anti-oxidation factors favors the oxidation) exerts harmful effects in living bodies. This oxidation reaction is evoked by a molecular species, called "ROS," which has a strong oxidative power generated in cells. Examples of the known ROS include hydrogen peroxide, singlet oxygen, hydroxyl radical, superoxide anion, and the like. As described above, the event that generates excessive ROS (i.e., oxidative stress) damages a molecule that is essential for normal activities of cells. As a result, ageing and diseases such as cancer, arteriosclerosis, myocardial infarction, and diabetes can probably be caused. Furthermore, the ROS is known as a substance responsible for a reperfusion injury occurring at the time of re-initiation of the blood flow in organs suffering from ischemia or a hypoxic condition. The present invention is useful for detection or prophylactic management of these diseases that oxidative stress influences.

As a marker protein or a regulatory factor, the native form of each protein may be used, and a molecule that is artificially modified in its part may also be used in order to improve the ability of the probe reagent. Examples of the artificially modified molecule include a molecule that lacks the C-terminal region of the marker protein, Nrf2. The deleted protein is desirable not to lose a regulatory factor-binding region and a ubiquitin-binding region, and substantially retains the native protein structure (conformation). The ability of the probe reagent includes, for example, the expression efficiency in cells, the strength of the binding between the marker protein and the regulatory factor, the speed and magnitude of the response to oxidative stress, and the like.

For oxidative stress-dependent degradation of the probe reagent of the present invention, the endogenous ubiquitin-proteasome system is utilized to degrade the probe reagent. Proteins that ubiquitin binds to is degraded by a proteasome, which is a proteinase complex. Since this degradation system is universally present in eukaryotic cells, all types of cells (e.g., animal cells including human cells, plant cells, yeast cells, fungi cells, etc.) and eukaryotes (e.g., animals (e.g., mammals other than human, birds, amphibians, reptiles, fish, insects, etc.), plants, yeast, fungi, etc.) can be a target for the measurement.

Specific examples of elements constituting the probe reagent of the present invention include, but are not limited to, the following.

Examples of a fluorescent protein that can be used include, but are not limited to, Aequorea victoria-derived GFP, EBFP, ECFP, EGFP, EYFP, and derivatives thereof, and also include coral-derived DsRed, HcRed, mCherry, and derivatives thereof However, any fluorescent proteins can be used. When excited by a laser beam, etc., these proteins emit fluorescence upon return to a ground state. Although being different depending on the types of the fluorescent proteins, a range of excitation wavelength is, for example, approximately 350 to 600 nm, and a range of emission wavelength is, for example, approximately 500 to 600 nm. Alternatively, luciferase, which is a firefly-derived enzyme catalyzing a bioluminescent reaction, may be disposed at the position of the fluorescent protein. In order to emit fluorescence from the fluorescent protein, it is necessary to be irradiated with an excitation light from outside. Accordingly, the measurement is difficult for a sample having strong intrinsic fluorescence or a sample in which the light irradiation affects its physiological activity. The luminescent method does not require excitation light irradiation, and allows proceeding the reaction by giving a chemiluminescent substrate such as luciferin to a cell. Thus, the method has an advantage that the measurement can be performed in a sample that is difficult to be irradiated with the excitation light. The above fluorescent or luminescent proteins are commercially available from Clontech, Roche Diagnostics, and the like.

Examples of a combination of the marker protein and the regulatory factor include a combination of human Nrf2 (GenBank Accession No. AAB32188) and Keap1 (GenBank Accession No. AAH21957), respectively. However, a combination of their homolog proteins having the same function, which proteins are derived from other species (e.g., animal species), may be used. If containing both a regulatory factor-binding site and a ubiquitin-binding site, only partial domains may be used as a marker protein, and can function as the probe reagent.

Nrf2 responds to oxidative stress in a cell, and functions as a transcription factor that induces expression of antioxidative proteins. Under the condition without oxidative stress in a cell, Nrf2 is localized in the cytoplasm in the form of binding to Keap1. At this time, Keap1 further binds to a ubiquitin ligase complex, thereby promoting ubiquitination of Nrf2. Since ubiquitinated Nrf2 is degraded by a proteasome that is a protease complex, its expression is inhibited. In contrast, when cells are exposed to oxidative stress, ROS reacts with Keap1, and alters the structure of Keap1. By this structural change, Keap1 dissociates from Nrf2, thereby inhibiting ubiquitination of Nrf2. The amount of Nrf2 is increased in a cell, initiating to exert its function as a transcription factor. Examples of Nrf2 target genes reported include cystine transporter, glutathione reductase, glutathione-S-transferase, glutathione reductase, glutathione peroxidase, peroxiredoxin, thioredoxin, and the like. Nrf2 protects a living organism from oxidative stress by regulating the expression of these genes. Keap1 is a factor that regulates an activity of Nrf2. The oxidative stress defense mechanism by Nrf2/Keap1 has been reviewed by Ken ITO, "Seikagaku" (Biochemistry) 78 (2), pp. 79-92 (2006) (Japan).

As described above, a marker protein that can be used in the present invention is preferably a protein (e.g., a transcription factor) regulating the expression of the genes that protect a living organism from oxidative stress. The regulatory factor is a protein that regulates an activity of the marker protein. Examples of other combinations of marker protein and regulatory factor include, for example, a combination of a maker protein detecting hypoxia, HIF1-α, and its regulatory factor, pVHL (Ohh, M. et al., Nat. Cell Biol. 2000, 2: 423-427). A hypoxia-inducible factor 1-α is abbreviated to HIF1-α, which is a transcription factor and is regulated by oxygen. That is, in the presence of oxygen at steady state HIF1-α protein is degraded by the ubiquitin-proteasome pathway. However, HIF1-α is known to function during hypoxia (e.g., angiogenesis, tumor formation, etc.). pVHL has been known as von Hippel-Lindau tumor suppressor, which binds to HIF1-α in an oxygen-dependent manner, and ubiquitinates HIF1-α.

A cleavage sequence is positioned between a regulatory factor and a fusion molecule comprising a fluorescent or luminescent protein and a marker protein, and comprises a cleavable sequence. In addition, when the foregoing reagent is cleaved at the cleavage sequence, the above regulatory factor and the fusion molecule are separated from each other. Preferred examples of such a cleavage sequence are a self-cleaved type peptide, include, for example, self-cleaved type 2A peptides (Szymczak, A L. et al., Nat. Biotechnol., 2004, 5: 589-594), and specifically include Thosea asigna virus 2A peptide (T2A) (SEQ ID NO: 8, EGRGSLLTCGDVEENPGP), and Porcine teschovirus-12A peptide (P2A) (SEQ ID NO: 9, ATNFSLLKQAGDVEENPGP). The cleavage site of these peptides locates between glycine (G) and proline (P) at the C-terminal side. The term "self-cleaved type peptide" used herein refers to the sequence of a peptide that is hydrolyzed during translation and is divided between G and P into two proteins.

According to a preferred embodiment, a probe reagent of the present invention is cleaved at the above cleavage sequence in a cell or an organism as described above, so that the above fusion molecule and the regulatory factor present separately. The separated regulatory factor changes its structure due to a reaction with ROS. The binding to or dissociation from the marker protein promotes or inhibits, respectively, degradation of the marker protein. Such a promotion or inhibition of degradation of the marker protein depends on the presence (or presence or absence) of oxidative stress and its level (or an amount or degree).

That is, if cells are not exposed to oxidative stress, the binding of the regulatory factor to the marker protein promotes ubiquitination of the marker protein, which is degraded by a proteasome. Simultaneously, the fluorescent or luminescent protein is also degraded, thereby failing to emit fluorescence or luminescence. In contrast, if cells are exposed to oxidative stress, the dissociation of the regulatory factor and the marker protein suppresses ubiquitination of the marker protein. As a result, fluorescence or luminescence is generated. In this case, a correlation can be seen between the degree of oxidative stress and the intensity of fluorescence or luminescence.

Additionally, the response of the probe reagent of the present invention to oxidative stress is reversible. This means that the fluorescent or luminescent intensity changes continuously from a relatively high state to a relatively low one, or changes to a baseline level at the time of a change from a state loaded with oxidative stress to a state without oxidative stress or a reduced state.

Specific examples of the probe reagent of the present invention include probe reagents as set forth below: the marker protein is Nrf2 protein, its homolog, or its analog having an equivalent activity; the regulatory factor is Keap1, its homolog, or its analog having an equivalent activity; the fluorescent or luminescent protein is any of the above proteins; and the cleavage sequence is any sequence that can be self-cleaved (e.g., the above T2A peptide). The configuration of these four elements is any of the four aspects shown in FIG. 1.

The term "homolog" used herein means a protein having an equivalent activity and property but derived from a different species. Examples of human Nrf2 homolog include, for example, Nrf2 derived from species excluding human, and specifically include mouse Nrf2, and the like. Similarly, examples of human Keap1 homolog include, for example, Keap1 derived from species excluding human such as mouse Keap1.

The term "analog" used herein means a mutant derivative in which an amino acid sequence of the natural or wild-type protein contains one or more (preferably one or several) amino acid deletions, substitutions, additions, or insertions, a chemically modified derivative having a modifier (e.g., sugar chain, acyl, alkyl, phosphate, or ADP-ribosyl), and the like. In the above, the term "several" means an integer of 2 to 10, for example, 2 to 8, 2 to 6, 2 to 5, 2 to 4, 2 to 3, and the like.

Alternatively, the above analog may be a mutant derivative having an amino acid sequence identity of 90% or more, preferably 93% or more, more preferably 95% or more, further preferably 98% or more, or 99% or more with the natural or wild-type protein. The term "identity" means a ratio (%) of the number of identical amino acids to the number of total amino acids with the proviso that two or more sequences are aligned by introducing gaps or without introducing gaps among those. The comparison of the identity among amino acid or nucleotide sequences (homology search, homology sequence search, etc.) can be carried out by using a known algorithm such as BLAST or FASTA (e.g., Altschul, S F. et al., J. Mol. Biol., 1990, 215(3): 403-410, etc.). The search can be performed by accessing a known database such as NCBI (GenBank), EMBL, and by using a procedure described in, for example, "How to use a database of genome net" edited by Toshihisa TAKAGI and Minoru KANEHISA, KYORITSU SHUPPAN Co., Ltd., Tokyo, Japan (1998).

In the above analog, the substitution of amino acids includes a conservative amino acid substitution, or a non-conservative amino acid substitution. The conservative amino acids refer to an amino acid group having a similar chemical property or structural property. Examples of the group are divided into, for example, a polar amino acid group (serine, threonine, asparagine, glutamine, cysteine, glycine, etc.), a hydrophobic amino acid group (alanine, leucine, isoleucine, valine, methionine, etc.), a basic amino acid group (lysine, arginine, histidine), an acidic amino acid group (glutamic acid, aspartic acid), a branched amino acid group (valine, isoleucine, leucine, etc.), an aromatic amino acid group (phenylalanine, tyrosine, tryptophan), and the like. On the other hand, the non-conservative amino acids refer to amino acids having a chemical or structural property different from each other. Preferred substitution is the conservative substitution.

Although the description is made on the proteins of the above homolog and analog, the similar explanation is also applied for the description on a nucleic acid (a DNA or an RNA). Such a nucleic acid can have a nucleotide sequence encoding the amino acid sequence of the above protein homolog or analog. In addition, examples of the nucleic acid analog include a mutant nucleic acid (e.g., a single nucleotide polymorphism, a splice variant, a silent mutation, etc.).

Figure 2:
FIG. 2 is the schematic diagram of a DNA structure encoding the fluorescent oxidative stress probe of the present invention.
Figure 3A:
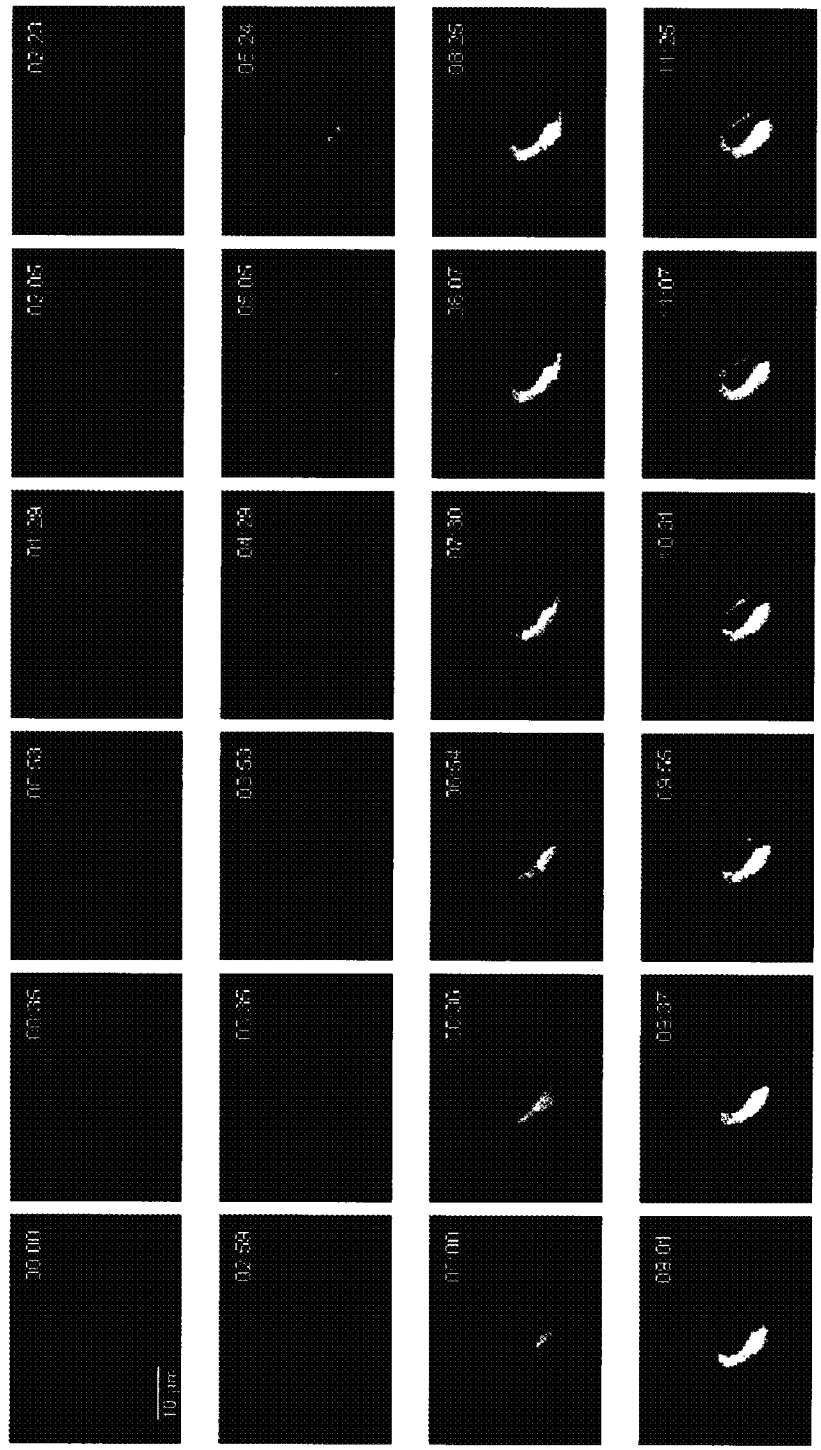
FIG. 3a shows changes over time of microscopic images (hour:minute) after DEM (diethylmaleate (which is an oxidative stress inducer)) was added at a concentration of 100 μM to a cell that the fluorescent oxidative stress probe of the present invention has been introduced into.
Figure 3B:
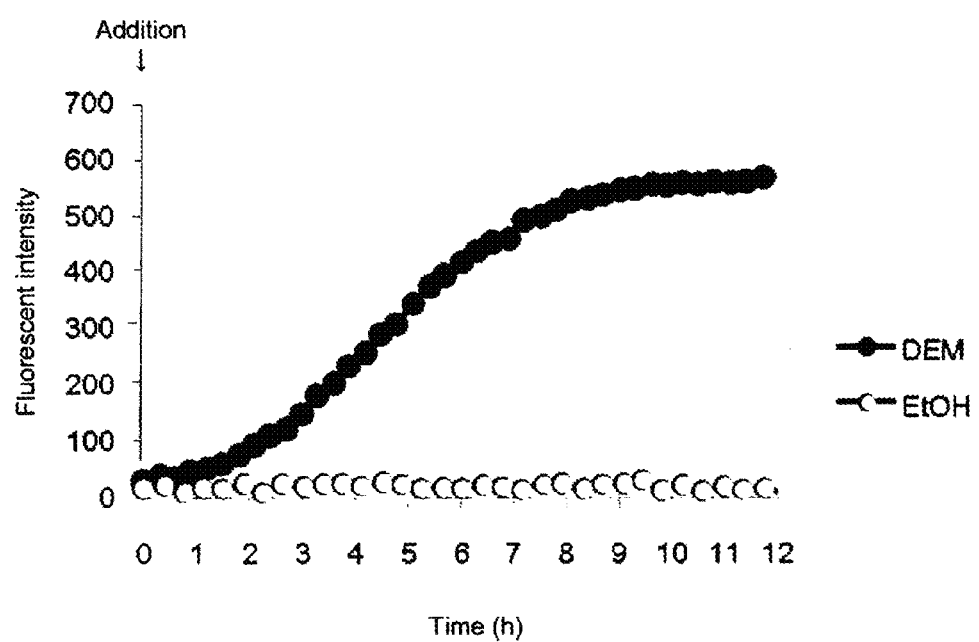
FIG. 3b is a graph showing changes over time of the fluorescent intensity after DEM (closed circle) was added at a concentration of 100 μM to a cell that the fluorescent oxidative stress probe of the present invention has been introduced into, or ethanol (EtOH) (open circle) was added thereto as a control at a concentration of 0.1%. The horizontal axis represents time (h), and the vertical axis represents fluorescent intensity.
Figure 4A:
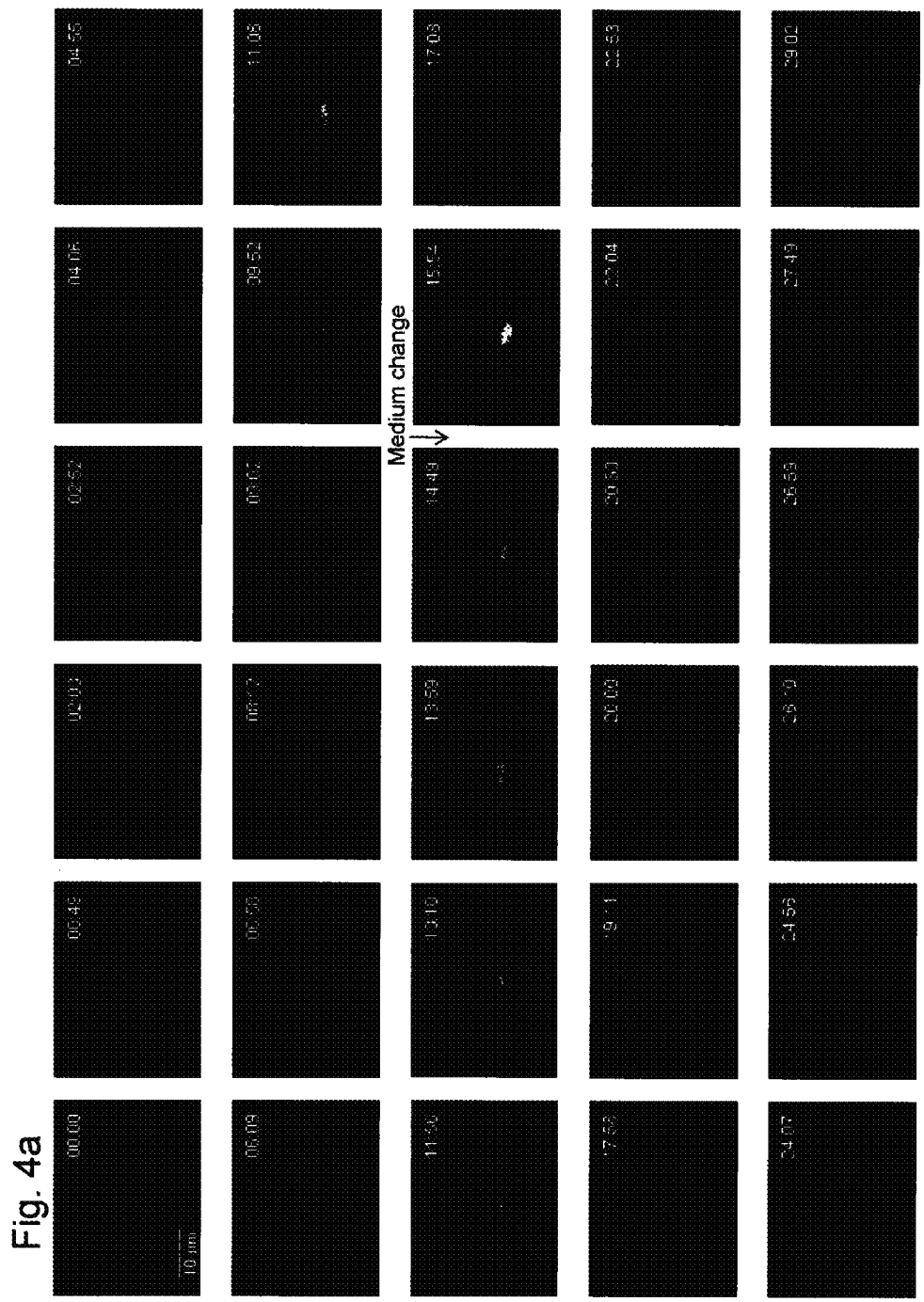
FIG. 4a shows changes over time of microscopic images (hour:minute) after DEM was added at a concentration of 100 μM to a cell that the fluorescent oxidative stress probe of the present invention has been introduced into. The medium was exchanged ("wash") to remove DEM 15 hours after the addition of DME.
Figure 4B:
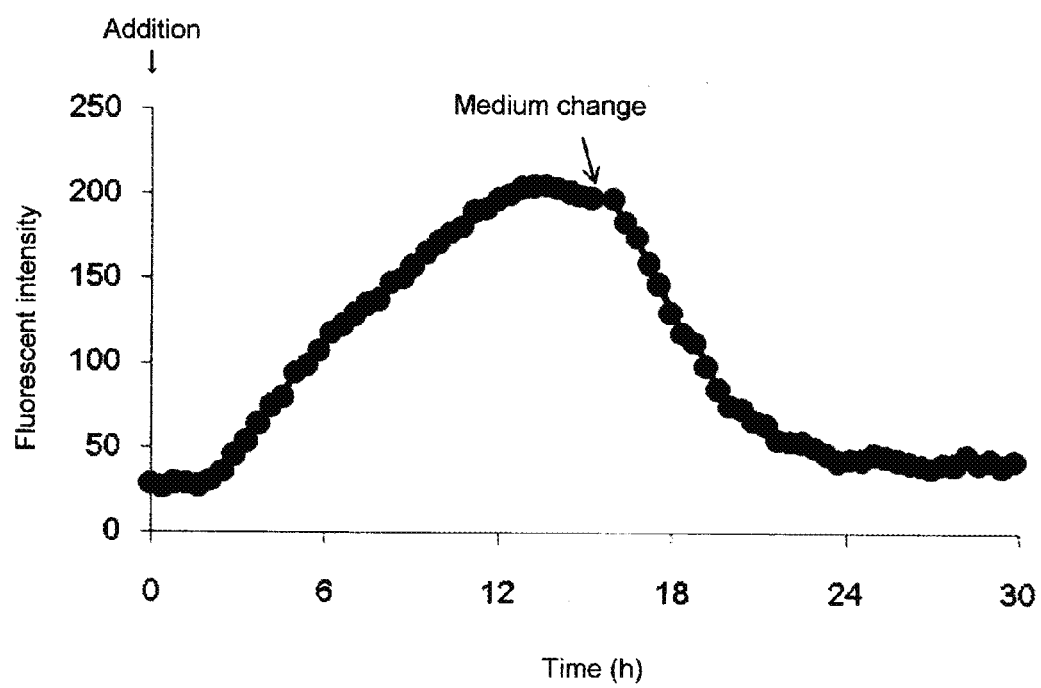
FIG. 4b shows changes over time of the fluorescent intensity after DEM was added at a concentration of 100 μM to a cell that the fluorescent oxidative stress probe of the present invention has been introduced into. The medium was exchanged ("wash") to remove DEM 15 hours after the addition of DEM. The horizontal axis represents time (h), and the vertical axis represents fluorescent intensity.
Figure 5A:
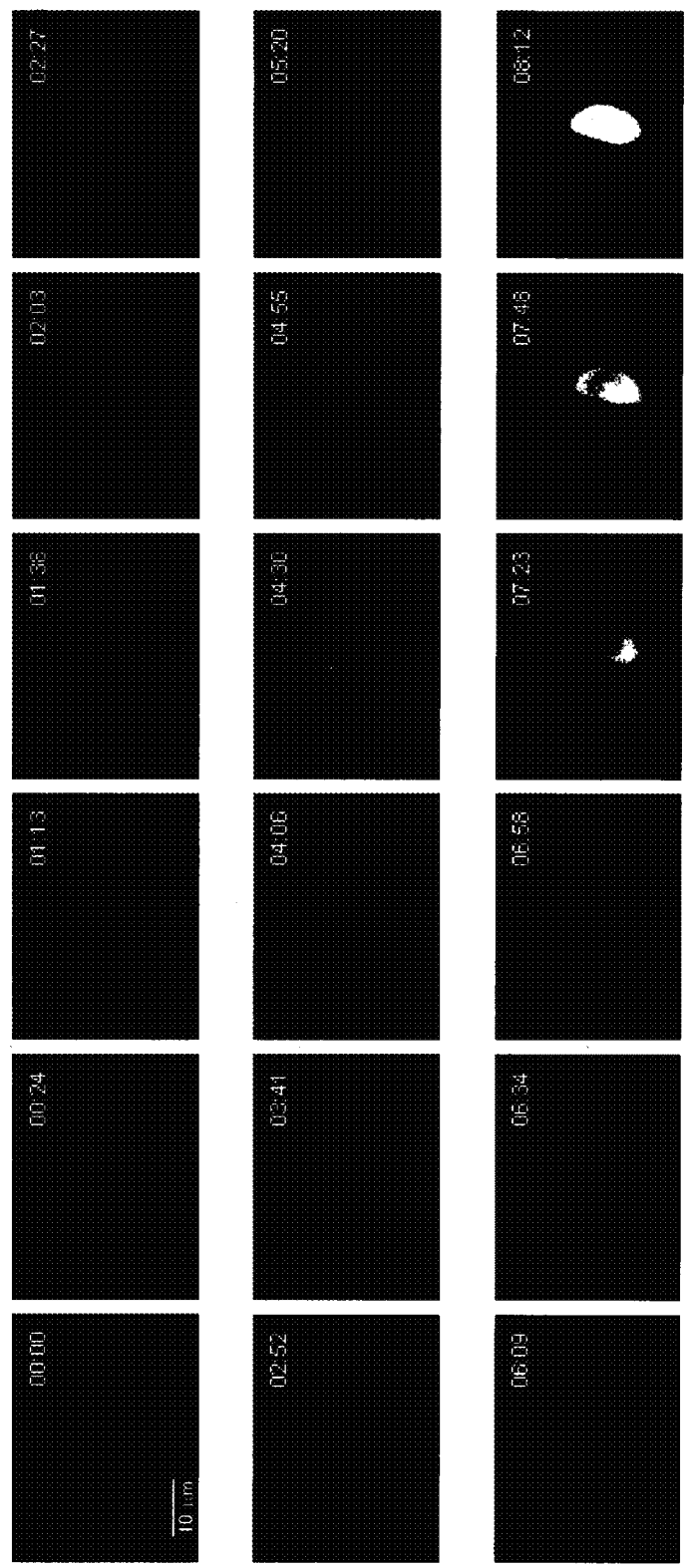
FIG. 5a shows changes over time of microscopic images (hour:minute) after MG132 (a proteasome inhibitor; Sigma Co.) was added at a concentration of 10 μM to a cell that the fluorescent oxidative stress probe of the present invention has been introduced into.
Figure 5B:
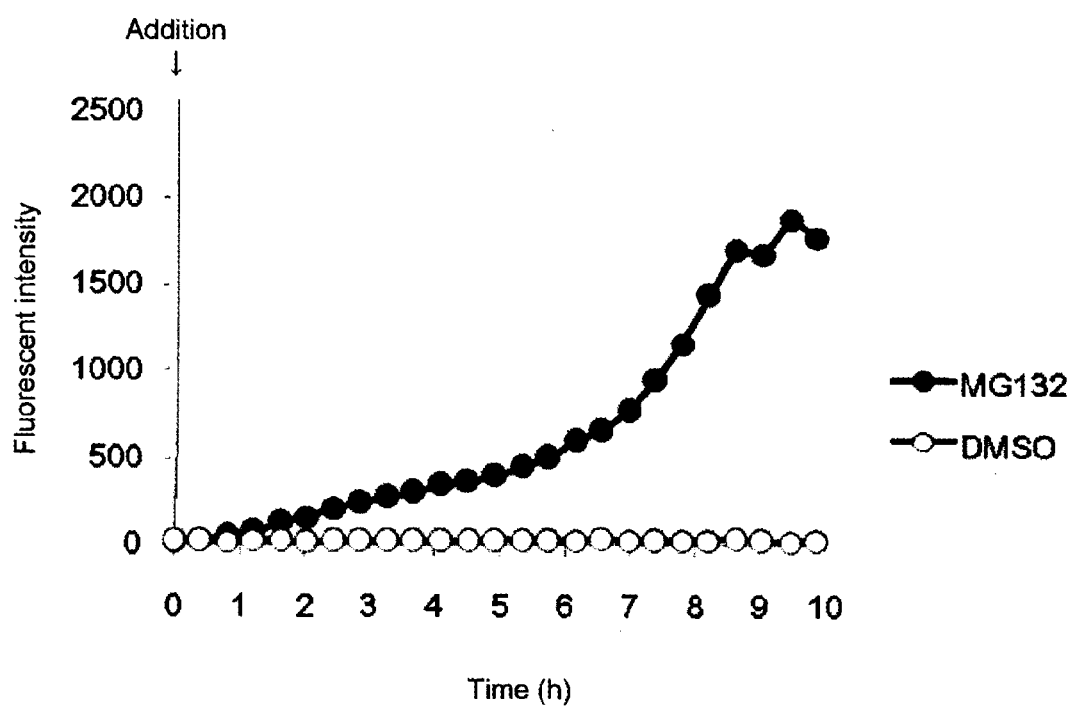
FIG. 5b is a graph showing changes over time of the fluorescent intensity after MG132 (closed circle) was added at a concentration of 10 μM to a cell that the fluorescent oxidative stress probe of the present invention has been introduced into, or DMSO (a control; open circle) is added thereto at a concentration of 0.1%. The horizontal axis represents time (h), and the vertical axis represents fluorescent intensity.

A more specific example of the probe reagent of the present invention is a fusion protein encoded by a DNA comprising the nucleotide sequence set forth in SEQ ID NO: 7 as described in the following examples (FIG. 2). When this DNA is introduced and can be expressed in a cell or an organism, the fusion protein is cleaved at the cleavage sequence into the fusion molecule and the regulatory factor so that an increase or decrease in the fluorescent intensity depending on an increase or decrease of oxidative stress can be observed (FIGS. 3 to 5). This probe allows the kinetics of oxidative stress in a cell or an organism to be measured in real-time.

The probe reagent of the present invention is usually used in the form of a fusion protein as described above. Thus, the reagent can be constructed by using genetic recombinant techniques. Details of such techniques are described in the following "2. Nucleic acid encoding a probe reagent". However, the expression of a DNA encoding the probe reagent can be carried out in both prokaryotic cells (e.g., E. coli, Bacillus bacteria, etc.) and eukaryotic cells.

2. Nucleic Acid Encoding a Probe Reagent

The present invention also provides a nucleic acid (a DNA or an RNA corresponding to the DNA) comprising a nucleotide sequence encoding an amino acid sequence of the probe reagent as defined and described in the above. As used herein, the RNA has a structure in which deoxyribose is replaced by ribose, and thymidine (T) by uracil (U), in the nucleotide sequence of the DNA. A preferred RNA is a mRNA corresponding to the DNA. The above DNA or RNA may further comprise one or more restriction enzyme sites to facilitate the recombinant operation in addition to nucleotide sequences encoding each of the above four elements.

Such DNA construct can be prepared by polymerase chain reaction (PCR) using specific primers, hybridization under stringent conditions using a specific probe, molecular cloning methods, etc. from cDNA libraries derived from appropriate tissues of an organism. For the cloning of human Nrf2 and Keap1, for example, the cDNA library can be prepared from tissues in which these genes are found to be expressed, such as small intestine, liver, and heart. The library can be prepared by a known method comprising: extracting total RNA from these tissues; further extracting mRNA; and synthesizing cDNA by using this mRNA as a template.

The PCR method comprises performing about 20 to 40 cycles of a set of the following steps. One cycle is defined as the steps comprising: denaturing a double-stranded DNA into a single-stranded DNA (e.g., about 94 to 98° C., 30 seconds to 2 minutes); annealing primers (e.g., 55° C., about 30 seconds to 1 minute); and elongating a DNA (e.g., about 72° C., 30 seconds to several minutes). The procedure may also further comprise a single denaturation step conducted at a similar temperature during a similar period of time before initiation of the all cycles, or a single elongation step at a similar temperature during a similar period of time after completion of the all cycles. The primers used for the PCR may preferably be: primers having a sequence identity of 90% or more, preferably 95% or more, and more preferably 98% or more with the sense strand or antisense strand of the template DNA; mix primers based on the amino acid sequence of the part of the intended protein; or random primes. The primers are preferably composed of a sense primer and an antisense primer. The size of these primers is usually 15 to 50 bases, and preferably 20 to 30 bases. The PCR is conducted in the presence of a heat-stable polymerase such as Taq polymerase and in a $Mg^{2+}$-containing PCR buffer. The practice of PCR becomes convenient if a commercially available PCR machine such as a thermal cycler (e.g., Perkin-Elmer, Bio-Rad, Applied Biosystems, TAKARA SHUZO CO., Ltd., etc.) is used. Specific examples of the PCR procedures are disclosed (see, Ausubel, F. M., et al, Short Protocols in Molecular Biology (2002), John Wiley & Sons; Siki, R A., et al., Science 1985, 230: 1350-1354; Erlich, H A., et al., Science 1991, 252: 1643-1651).

The hybridization method uses a probe having a sequence complementary to the nucleotide sequence of a known intended DNA or having a sequence identity of 90% or more, preferably 95% or more, and more preferably 98% or more with the complementary nucleotide sequence. The method uses a probe having the length of 20 or more nucleotides, preferably 30 or more nucleotides, and more preferably 50 or more nucleotides (e.g., 60 to 200 nucleotides, 60 to 150 nucleotides, or 60 to 100 nucleotides), and performs hybridization under stringent conditions. Examples of the stringent conditions can include, for example, a condition comprising: hybridizing at 40 to 50° C. under 2 to 6×SSC (sodium chloride/sodium citrate), and thereafter; and washing one or more times by using 0.1 to 0.2×SSC and 0.1% SDS at 50 to 65° C. Specific examples of a hybridization procedure are disclosed above by F. M. Ausubel et al (ibid).

A DNA of the present invention comprises a DNA encoding the above first probe reagent or second probe reagent. A specific example is a DNA comprising the nucleotide sequence set forth in SEQ ID NO: 7.

The present invention further provides a vector comprising the above DNA and a regulatory sequence that allows expressing the DNA.

Examples of the vector that is suitable for DNA expression in a host cell preferably include a vector for cells, particularly eukaryotic cells, for example, animal cells (mammalian cells including human cells, bird cells, fish cells, insect cells, etc.), plant cells (monocotyledonous plant cells, dicotyledonous plant cells, etc.), yeast cells, fungi cells (filamentous fungi, basidiomycetes, etc.) and the like. As such vectors, any vectors that are commercially available or are described in a publication, can be used. Examples of the vectors can include plasmid vectors (e.g., pUC series, pBluescript series, pBR series, etc.), and viral vectors (e.g., adenovirus, adeno-associated virus, retrovirus, etc.). Examples of the vectors that can be used in plant cells include binary vectors (e.g., pBI series plasmids) containing the left and the right borders (LB and RB) of T-DNA region, Ti plasmid, and the like.

The vectors can comprise a variety of regulatory sequences for DNA expression. Examples of the regulatory sequences can include, for example, a promoter, a promoter/enhancer, a ribosome-binding sequence, a terminator, and the like. Examples of the promoter can include virus-derived promoters (e.g., SV40, CMV, RSV, CaMV, etc.), promoters for glycolysis enzymes (e.g., enolase, glyceraldehyde-3-phosphate dehydrogenase, hexokinase, pyruvate decarboxylase, phosphofructokinase, pyruvate kinase, etc.). In addition, the vectors can comprise a selection marker sequence for selection of a recombinant. Examples of the marker can include, for example, drug-resistance genes (e.g., an ampicillin resistance gene, a kanamycin resistance gene, a neomycin resistance gene, etc.), dominant selection markers (e.g., dihydrofolate reductase, thymidine kinase, adenosine deaminase, etc.), auxotrophic complementary selection markers (e.g., HIS3, LEU2, TRP1, URA3, etc.), and the like.

When a DNA encoding the probe reagent of the present invention is introduced into a cell, the DNA is expressed to produce the probe reagent in the cell. Examples of a method that introduces DNA (in some cases, RNA) into a cell can include, for example, a liposome-mediated method such as lipofection, electroporation, microinjection, calcium phosphate method, *Agrobacterium* method, a gene bombardment method, and the like. These methods are described in, for example, Watson's 2nd Edition "Recombinant DNA: Genes and Genomes-A Short Course" (1994), Maruzen, Tokyo, Japan, in which the translation is supervised by Michio MATSUHASHI.

3. Measurement of Oxidative Stress

The present invention further provides a method of measuring oxidative stress in a cell or an organism, the method comprising: introducing the above probe reagent or the above vector into a cell or a eukaryote (excluding human); and measuring oxidative stress based on a fluorescent or luminescent intensity in the cell or the organism.

Alternatively, the present invention provides a method of measuring oxidative stress in a cell or an organism excluding human, the method comprising the steps of:

introducing the fusion molecule or a vector comprising a nucleic acid encoding the fusion molecule in the cell or the organism, thereby localizing the fusion molecule in the cell or the organism, wherein the fusion molecule comprises a fluorescent or luminescent protein and a marker protein whose degradation is regulated depending on degrees of the oxidative stress in the cell or the organism; and measuring an amount of fluorescent or luminescent derived from the fluorescent or luminescent protein to determine the presence of or a level of the oxidative stress in the cell or the organism based on a degree of regulation of degradation of the fusion molecule, wherein the marker protein comprises a regulatory factor-binding site and a ubiquitin-binding site, and the degradation of the fusion molecule is regulated by a regulatory factor in response to ROS.

In a method of the present invention, the fusion molecule and the regulatory factor may be placed under the condition in which these are expressed at least in the same cell. In some cases, these may be introduced, for example, into separate vectors in which a DNA encoding the fusion molecule and a DNA encoding the regulatory factor are inserted. Of course, when the transfection efficiency and the easiness of regulation of the expression are taken into consideration, more preferred is to introduce these molecules into a single vector in which DNAs encoding these are inserted.

Besides, the regulatory factor can use an endogenous (or intrinsic) molecule in the cell (i.e., a molecule that a cell possesses in nature) as well as an exogenous molecule as described above. In addition, a combination of the regulatory factor and the marker protein, if the interaction is regulated in response to a degree of oxidative stress, may be a combination of these derived from any organism species, and preferably derived from the same (i.e., cognate) species.

One of the features of the present invention is a feature that the measurement can be carried out in real-time. During the time, if the regulatory factor is a molecule in which its structure change is reversible in the reaction with ROS, the response of the probe reagent to oxidative stress is also reversible. Examples of a combination of the probe reagent and the regulatory factor exerting such an effect include the Nrf2-Keap1 system as demonstrated in Examples. Since the above response is reversible, the removal of oxidative stress reduces a fluorescent or luminescent intensity while the reception of oxidative stress in a cell or an organism gradually increases the fluorescent or luminescent intensity. Accordingly, the fluorescent or luminescent intensity can be measured in real-time depending on the increase or decrease of the oxidative stress (FIG. 4a and FIG. 4b).

Examples of a cell that can be used in the present invention, as described above, include eukaryotic cells such as vertebrate cells (e.g., mammalian cells (including human cells)), invertebrate cells (e.g., insect cells), plant cells, algae cells, yeast cells, fungus cells, and the like. Examples of the cell also include oocytes, embryonic stem (ES) cells, spermatogoniums, primordial germ cells, and pluripotent stem cells such as induced pluripotent stem (iPS) cells, and the like.

Examples of organisms (excluding human) that can be used in the present invention include animals (e.g., vertebrates including mammals, invertebrates, etc.), plants (e.g., monocotyledonous plants, dicotyledonous plants, etc.), yeasts, fungi, and the like. Examples of the animals or plants also include transgenic animals (excluding human) and transgenic plants.

In order to make the probe reagent of the present invention function properly, in principle, the probe reagent is required to be expressed continuously during the measurement. When a measurement is carried out during a prolonged period of time, it is desirable to express the probe reagent by linking with a promoter that induces a stable expression of the gene. For this purpose, examples of vectors that can be used include autonomously replicable vectors that can express a DNA encoding a probe reagent, artificial chromosomes (e.g., HAC, BAC, YAC, etc.) in which the DNA is incorporated, or vectors for incorporating the DNA in the genome of a cell by homologous recombination. As well as a method that allows the probe reagent to be transiently expressed in a cell as described above, a cell keeping the gene and stably expressing the probe reagent may be created and used for the measurement.

Since the probe reagent of the present invention changes the fluorescent or luminescent intensity in response to the strength of oxidative stress, the generation of a transgenic organism into which a transgene containing a DNA encoding this probe reagent is introduced makes it possible to measure oxidative stress not only at a cellular level but also at an organism level. In this occasion, by linking the transgene downstream of an appropriate promoter, it is possible to use the organism for the measurement under the condition in which the transgene is selectively expressed in the intended organ or tissue.

For the generation of a transgenic animal (excluding human), for example, a nuclear transfer method and a method using pluripotent stem cells such as ES cells and iPS cells can be available. These methods are described briefly as follows.

The nuclear transfer method, for example, comprises: introducing a transgene into the genome of a somatic cell such as a fibroblast; thereafter, microinjecting a nucleus removed from the cell into an enucleated fertilized egg or unfertilized egg; transplanting these eggs into the uteri or oviducts of host animals; developing and giving them birth; and obtaining a chimeric animal.

The method utilizing ES cells comprises: introducing a transgene into an inner cell mass from blastcysts or 8-cell-stage embryos after fertilization of an animal (excluding human) by using microinjection, microcell fusion, electrofusion, etc.; thereafter, obtaining an transplanted embryo by injecting ES cells into another blastocyst; transplanting these embryos into the uteri of host animals; giving them birth; and obtaining a chimeric animal (e.g., "Chromatin-chromosome experimental protocols" (2004), edited by Mitsuo OSHIMURA, YODOSHA CO., LTD., Tokyo, Japan).

The chimeric animal produced as described above further mates with a wild type animal of the same species, and furthermore obtained heterozygotes mate with each other to obtain homozygous offspring animals (excluding human).

The iPS cells are pluripotent stem cells that can be obtained by introducing transcription factors (e.g., Oct4, Sox2, Klf4, c-Myc, etc.) or DNAs (may be mediated via a vector) encoding the factors into a somatic cell of a mammal, and by culturing the cell. The iPS cells are known to be able to contribute to a germline (Takahashi, K. and Yamanaka, S. (2006) Cell 126: 663-676).

The transgene is a construct (vector) in which a DNA sequence of the present invention (SEQ ID NO: 7) is inserted, for example, between about 2-7 kb DNA sequences homologous to 5' and 3' untranslated regions of Nrf2 gene. Alternatively, a DNA sequence of the present invention or Nrf2 gene may be introduced into artificial chromosomes (HAC, YAC, BAC, etc.). The construct or the artificial chromosome can further optionally comprise a drug-resistant gene, a promoter/enhancer, an IRES, a poly-A sequence, a terminator, or the like.

Besides, for the generation of a transgenic plant, there is provided a method comprising: introducing a vector comprising a DNA of the present invention into a tissue such as leaf and stem by using the Agrobacterium method, particle gun method, or the like; thereafter, inducing a callus formation; and regenerating plant bodies.

In the transgene, a DNA encoding luciferase, which is a firefly-derived enzyme catalyzing a bioluminescent reaction, may be disposed at the position of the fluorescent protein of the probe reagent. In order to emit fluorescence from the fluorescent protein, it is necessary to be irradiated with an excitation light from outside. Accordingly, the measurement is difficult for a sample having strong intrinsic fluorescence or a sample in which the light irradiation affects its physiological activity. The luminescent method does not require excitation light irradiation, and can proceed the reaction by applying a chemiluminescent substrate such as luciferin to a cell or an organism. Thus, the measurement can be performed in a sample that is difficult to be irradiated with the excitation light.

Examples of another method in which a probe reagent is introduced into a cell of an animal include, for example, a method utilizing a cationic liposome (e.g., intravenous administration, etc.). In this method, a negative charge on cell surface and the cationic liposome attract each other to form a fusion body. Then, the probe reagent enters the cell by means of internalization.

In addition, the examples include a method comprising: generating a cell that keeps a DNA of a probe reagent and stably expresses the probe reagent; and transplanting the cell into an animal.

For the measurement using a probe reagent or a DNA of the present invention, a common fluorescent or luminescent measurement device can be used. For the measurement at a single cell level, a microscopic imaging apparatus can be used. On the other hand, for the measurement at an organism level or the measurement using a microplate, an imaging apparatus that is equipped with a dark box for a macroscopic view can be used. Dynamics of oxidative stress can be measured in real-time in a living sample by using a device with a time-lapse imaging function.

4. Screening an Oxidative Stress-Regulating Substance

The present invention further provided a method of screening an oxidative stress-regulating substance, the method comprising:
introducing a candidate substance and the above probe reagent or the above vector in a cell or an organism (excluding human) being loaded with oxidative stress; and
screening the substance decreasing or increasing a fluorescent or luminescent intensity in the cell.

Species of a cell or an organism (a transgenic animal excluding human) that can be used in this method are exemplified above. The generation of a transgenic animal is also described above.

Examples of the candidate substance include any substances (e.g., small molecules (organic molecules or inorganic substances), proteins, peptides, saccharides, lipids, etc.), known pharmaceutical agents, and the like.

When a cell is used for the screening, the candidate substance is added to a medium. In contrast, when an organism is used for the screening, the candidate substance is ingested or administrated (e.g., orally, intravenously, intrarectally, subcutaneously, intramuscularly, or transmucosally) to the organism.

An effect of the candidate substance during the periodic loaded with oxidative stress in a cell or an organism is evaluated by measuring the fluorescent intensity that is emitted by being excited with a specific wavelength of light. If the fluorescent intensity is reduced or decreased to a baseline level by action of the candidate substance, the substance can be presumed to be an oxidative stress-suppressing substance.

An oxidative stress-suppressing substance that is found by the method of the present invention will be useful in prophylaxis and treatment of organs, etc. suffering from, for example, aging, ischemia, hypoxia, or diseases (e.g., cancer, arteriosclerosis, myocardial infarction, diabetes, etc.), which are caused by oxidative stress.

5. Kit

The present invention further provides a kit for measuring oxidative stress or screening an oxidative stress-regulating substance, the kit comprising at least one member selected from the group consisting of the above probe reagents, the above DNAs or RNAs, and the above vectors.

The kit can comprise a buffer(s), a substrate(s), or an instruction(s), in addition to ingredients put or sealed in different containers.

EXAMPLES

Hereinafter, although the present invention is described by Examples, the scope of the present invention is not limited to these Examples.

Example 1

Design of a Probe Reagent

As an example of a probe reagent having the feature described above, a probe reagent for measuring oxidative stress was prepared using mKO2 as a fluorescent protein, Nrf2 as a marker protein, and Keap1 as a regulatory factor. In this reagent, as oxidative stress increased, the degradation of the probe reagent reduced, thereby increasing the fluorescent intensity.

First, intrinsic kinetics of Nrf2 and Keap1 in a cell is explained. Nrf2 responds to oxidative stress in a cell, and functions as a transcription factor that induces expression of antioxidative proteins responsible for the defensive functions against this oxidative stress. Under the condition without oxidative stress in a cell, Nrf2 is present in the cytoplasm in the form of binding to Keap1. At this time, Keap1 further binds to a ubiquitin ligase complex, thereby promoting ubiquitination of Nrf2. Since ubiquitinated Nrf2 is degraded by a proteasome that is a protease complex, the increase of Nrf2 is inhibited. In contrast, when cells are exposed to oxidative stress, ROS reacts with Keap1, and alters the structure of Keap1. Due to this structure change, Keap1 dissociates from Nrf2, thereby inhibiting ubiquitination of Nrf2. The amount of Nrf2 is increased in a cell, initiating to exert its function as a transcription factor.

The structure of a probe reagent (mKO2-Nrf2_100-T2A-Keap1) constructed was shown in FIG. 2. The reagent had a structure in which, from the N-terminus, a fluorescent protein (mKO2), a domain of Nrf2 (1 to 100 amino acids from the N-terminus) that comprised a Keap1-binding site and a ubiquitin-binding site, a self-cleaved peptide (T2A), and Keap1 were ligated in a line. Here, mKO2 derived from a species of coral, *Fungia scutaria*, was used as a fluorescent protein. However, other fluorescent proteins may be used. Examples of the fluorescent proteins included *Aequorea victoria*-derived EBFP, ECFP, EGFP, EYFP, etc. and the derivatives thereof, and also include coral-derived DsRed, HcRed, mCherry, etc. and the derivatives thereof. As a marker protein and a regulatory factor, human-derived Nrf2 and Keap1, respectively, were used. However, a combination of proteins deriving from other species and having the same function could be used. Here, only some of the domains of Nrf2 were used as a marker protein. However, any molecules comprising both a regulatory factor-binding site and a ubiquitin-binding site could function as a probe reagent. The size of Nrf2 used herein was optimized by measuring an amount of expression of the probe reagent in a cell and by evaluating a capability in response to oxidative stress.

Example 2

Preparation of cDNA cDNA encoding a gene of a probe reagent was prepared by the following procedures. This cDNA was inserted into a plasmid for introducing itself into a cell.

Nrf2 and Keap1 genes were cloned from a human heart cDNA library. Sense primer (SEQ ID NO: 1) and antisense primer (SEQ ID NO: 2), and PrimeSTAR enzyme (manufactured by TAKARA Bio Co., Ltd.) were used to perform a PCR reaction to amplify a nucleic acid encoding the amino acids 1-100 of Nrf2 by using the Nrf2 gene as a template. The sense primer contained a cleavage site for XhoI. The antisense primer contained a nucleotide sequence of T2A peptide and a cleavage site for HindIII. In addition, sense primer (SEQ ID NO: 3) and antisense primer (SEQ ID NO: 4), and PrimeSTAR enzyme were used to perform a PCR reaction using Keap1 gene as a template. The sense primer contained a cleavage site for HindIII. The antisense primer contained a cleavage site for XbaI.

Both the ends of the PCR product amplified using Nrf2 as a template were cleaved by restriction enzymes, XhoI and HindIII. Both the ends of the PCR product amplified using Keap1 as a template were cleaved by restriction enzymes, HindIII and XbaI. The cleaved PCR product was inserted into XhoI-XbaI cleavage sites of pcDNA3 (manufactured by Invitrogen), which is a plasmid used for expression in a cell.

Sense primer (SEQ ID NO: 5) and antisense primer (SEQ ID NO: 6) were used to amplify a nucleic acid encoding mKO2 protein by PCR (PCR conditions: denaturation at 98° C. for 10 seconds; annealing at 55° C. for 30 seconds; extension at 72° C. for 1 minute). The sense primer contained a cleavage site for EcoRI. The antisense primer contained a cleavage site for EcoRV. Both the ends of the PCR product were cleaved by restriction enzymes, EcoRI and EcoRV. The cleaved PCR product was inserted into the EcoRI-EcoRV cleavage sites of pcDNA3 (FIG. 2).

```
SEQ ID NO: 1:
GGCCTCGAGATGATGGACTTGGAGCTGCCG

SEQ ID NO: 2:
AAGCTTTGGGCCAGGATTCTCCTCGACGTCACCGCATGTTAGAAGACTT

CCTCTGCCCTCGGCAGATCCACTGGT

SEQ ID NO: 3:
CCGTAAGCTTATGCAGCCAGATCCCAGG

SEQ ID NO: 4:
GCTCTAGATTAACAGGTACAGTTCTG

SEQ ID NO: 5:
GGGGAATTCGCCACCATGGTGAGTGTGATTAAACCAGAG

SEQ ID NO: 6:
ATGGATATCCGCCCTGGGAAGGCAACATTGAGTAATGAGCTACTGCATC

TTCTAC
```

Example 3

Evaluation of a Probe Reagent by Imaging of a Cell

The prepared cDNA was transfected into HeLa cells that were cultured on a glass bottom dish by using FuGENE HD (manufactured by Roche Applied Science). The medium was replaced by the fresh medium 12 hours after the transfection. After 24 hours, fluorescence was observed with an incubator microscope (Olympus Corporation, LCV 100). This microscope was equipped with a cooled CCD camera so that fluorescent images of a cell were able to be captured over time. Before the experiment, only fluorescence at the background light level was detected even in a cell that expressed the probe reagent. This demonstrates that almost all of the probe reagent in the cell was degraded under stable conditions without being loaded with oxidative stress.

In order to verify that the constructed probe reagent responded correctly to oxidative stress as intended, diethylmaleate (DEM), which is an oxidative stress inducer, was added at a concentration of 100 µM, and the fluorescent intensity of mKO2 (ex; BP520-540HQ, em; BP555-600HQ) was measured. After the addition of DEM, a more than 10 times increase in the fluorescent intensity of mKO2 was observed (FIG. 3). When ethanol, a solvent, was added at 0.1% as a control, the fluorescent intensity of mKO2 was not increased. The above results demonstrated that the fluorescent intensity of this probe was increased in an oxidative stress-dependent manner. Furthermore, when the DEM added was washed away, the fluorescent intensity of mKO2 was decreased to the baseline state (FIG. 4). This demonstrates that the response of this probe reagent to oxidative stress was reversible.

In order to verify that this probe reagent was degraded by a proteasome in a cell under conditions without being exposed to oxidative stress, an experiment using a proteasome inhibitor, MG132, was carried out. When MG132 was added at a concentration of 10 µM, a subsequent increase in the fluorescent intensity of mKO2 was observed. In contrast, after dimethylsulfoxide (DMSO), a solvent, was added at 0.1% as a control, the fluorescent intensity of mKO2 was not increased (FIG. 5). The above results demonstrated that this probe reagent was degraded by a proteasome when the cell was not exposed to oxidative stress.

Example 4

Evaluation of a Probe Reagent by Western Blotting

In order to confirm that this probe reagent was modified in a cell as originally designed, an experiment using Western blotting was conducted.

Figure 6:
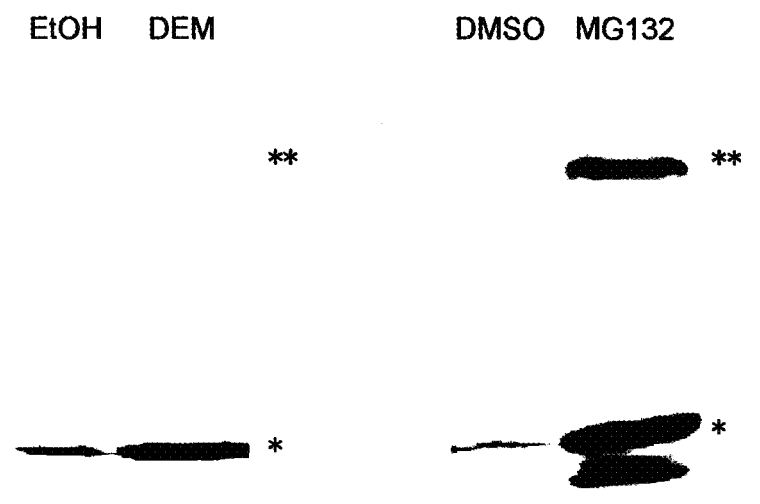

First, to confirm that this probe reagent was separated into an mKO2-Nrf2 fusion molecule and Keap1 by the T2A peptide in a cell, the following experiments were performed. The cDNA, which was prepared using FuGENE® HD (Roche Applied Science Inc.), was transfected into HeLa cells cultured on a 35-mm dish. The medium was replaced by the fresh medium 12 hours after the transfection. After the 12 hours, DEM was added at a concentration of 100 µM, and ethanol was added at 0.1% as a control. The cells were cultured for further 8 hours. After that, Western blotting was conducted by using an anti-Nrf2 antibody (Santa Cruz Inc.). Both in the case of adding DEM and the case of adding ethanol, the band of the mKO2-Nrf2 fusion molecule was detected, but the band of the probe reagent comprising linked Keap1 was hardly observed. This result demonstrated that this probe reagent was separated into the mKO2-Nrf2 fusion molecule and Keap1 by the T2A peptide in the cell. Additionally, in the case of adding DEM, the strong band was detected compared to the case of adding ethanol. This result demonstrates that the amount of the probe reagent increased due to oxidative stress induced by DEM (FIG. 6).

Next, the fact that this probe reagent was degraded by a proteasome in a cell was confirmed by performing Western blotting. A proteasome inhibitor, MG132, was added at a concentration of 10 µM to HeLa cells that had been cultured in a similar manner. DMSO was added at 0.1% to control cells as well. In the case of adding MG132, the strong band was detected compared to the case of adding DMSO. This result indicates that the amount of the probe reagent in the cells increased. This result demonstrates that this probe reagent was degraded by a proteasome under conditions without being exposed to oxidative stress (FIG. 6).

INDUSTRIAL APPLICABILITY

The present invention provides a probe reagent allowing the kinetics of oxidative stress in a cell or an organism to be measured in real-time. In order to construct a fluorescent or luminescent probe having superior detection sensitivity, it is important to increase a signal at the response or to decrease a signal at the time without the response. The probe reagent of the present invention is either a probe reagent comprising a fusion molecule comprising a fluorescent or luminescent protein and a marker protein, or a probe reagent comprising, in the same probe, the fusion molecule and a regulatory factor that promotes degradation of the fusion molecule by a proteasome. For the latter case, the regulatory factor can be cleaved and separated from the probe in the cell, thereby exerting an effect on the marker protein. Otherwise, the regulatory factor can act on the marker protein under the condition that the regulatory factor is not separated from the probe.

In the present invention, preferred is a probe reagent that comprises the fusion molecule and the regulatory factor in the probe, and that can be cleaved and separated between the fusion molecule and the regulatory factor. By using this probe reagent, the fluorescent signal can be reduced to the background light level at the time without the response. As a result, an increase in the fluorescent signal at the response becomes dynamic compared to a conventional method so that there can be provided a probe reagent having a much superior detection sensitivity. Thus, the ability of the probe reagent to precisely detect an extremely small change in oxidative stress is effective in detecting an initial stage at which oxidative stress occurs. This ability is also effective for measuring the oxidative stress even in a deep part of the body of an animal individual in which it is difficult to measure a difference in extremely small quantities of light due to light scattering or autofluorescence in a tissue.

It was demonstrated that the response of a probe reagent of the present invention to oxidative stress is reversible. Therefore, the probe reagent makes it possible to measure the oxidative stress either under the condition of promoting oxidative stress or under the condition of suppressing oxidative stress. Accordingly, screening of an oxidative stress-causing substance or an oxidative stress-suppressing substance can be carried out by using the single reagent. Since the response is reversible, the probe reagent can perform the measurement with different kinds and varied amounts of agents that are administered to a single biological sample. This feature makes it possible to reduce the number of the biological samples used in the experiment, and also makes the measurement using the same samples possible so that the comparison of the results can be performed easily and precisely.

The present invention is useful in clarifying a mechanism of the ageing or diseases which are associated with oxidative stress, and is also useful in the fields of industry and medicine (e.g., screening of candidate agents suppressing these ageing and diseases, etc.).

All of the publications, patents, and patent applications cited herein are incorporated herein by reference in their entirety.

SEQUENCE LISTING FREE TEXT

SEQ ID NO: 7: DNA sequence of mKO2-Nrf2__100-T2A-Keap1

The invention claimed is:

1. A fluorescent or luminescent probe reagent for measuring oxidative stress in a cell or an organism, the reagent being a fusion protein comprising:
   a fluorescent or luminescent protein;
   a marker protein;
   a cleavage sequence; and
   a regulatory factor,
   wherein
   the marker protein makes it possible to detect the oxidative stress caused by reactive oxygen species, and comprises a regulatory factor-binding site and a ubiquitin-binding site;
   the regulatory factor is a protein capable of regulating degradation of the marker protein in response to the reactive oxygen species;
   the fluorescent or luminescent protein and the marker protein are adjacent to each other in any order so as to form a fusion molecule;
   the cleavage sequence is positioned between the fusion molecule and the regulatory factor and comprises a cleavable sequence
   that is cleaved in the cell or the organism, so that the reagent comprises a protein containing the fusion molecule and a protein containing the regulatory factor separated at the cleavage sequence; and
   binding or dissociation between the regulatory factor and the marker protein promotes or reduces the degradation of the marker protein, and
   wherein the fusion protein comprises the components positioned from N-terminus to C-terminus in one of the following orders:
   (1) the fluorescent or luminescent protein, the marker protein, the cleavage sequence, and the regulatory factor;
   (2) the marker protein, the fluorescent or luminescent protein, the cleavage sequence, and the regulatory factor;
   (3) the regulatory factor, the cleavage sequence, the fluorescent or luminescent protein, and the marker protein; and
   (4) the regulatory factor, the cleavage sequence, the marker protein, and the fluorescent or luminescent protein.

2. The probe reagent according to claim 1, wherein the fluorescent or luminescent protein is selected from coral or *Aequorea victoria*.

3. The probe reagent according to claim 1, wherein the luminescent protein is luciferase.

4. The probe reagent according to claim 1, wherein the marker protein and the regulatory factor are human Nrf2 (Accession No. AAB32188) and human Keap1 (Accession No. AAH21957), respectively.

5. A DNA or RNA encoding the probe reagent according to claim 1.

6. The DNA according to claim 5, wherein the DNA comprises the nucleotide sequence shown in SEQ ID NO: 7.

7. A vector comprising the DNA according to claim 5.

8. The vector according to claim 7, further comprising a regulatory sequence.

9. A method of measuring oxidative stress in a cell, the method comprising:
   introducing the probe reagent according to claim 1 or the vector according to claim 7 into a cell or an organism excluding human; and
   measuring the oxidative stress based on fluorescent or luminescent intensity in the cell or the organism.

10. The method according to claim 9, wherein the measurement is performed in real-time.

11. A method of screening for an oxidative stress-regulating substance, the method comprising:
    introducing a candidate substance and the probe reagent according to claim 1 or the vector according to claim 7 into a cell or organism, excluding human, which has been loaded with oxidative stress; and
    screening for a substance which decreases or increases a fluorescent or luminescent intensity in the cell or organism.

12. A kit for measuring oxidative stress or screening an oxidative stress-regulating substance, the kit comprising a fluorescent or luminescent probe reagent for measuring oxidative stress in a cell or an organism, the reagent being a fusion protein comprising:
    a fluorescent or luminescent protein;
    a marker protein;
    a cleavage sequence; and
    a regulatory factor,
    wherein
    the marker protein makes it possible to detect the oxidative stress caused by reactive oxygen species, and comprises a regulatory factor-binding site and a ubiquitin-binding site;
    the regulatory factor is a protein capable of regulating degradation of the marker protein in response to the reactive oxygen species;

the fluorescent or luminescent protein and the marker protein are adjacent to each other in any order so as to form a fusion molecule;

the cleavage sequence is positioned between the fusion molecule and the regulatory factor, and comprises a cleavable sequence that is cleaved in the cell or the organism, so that the reagent comprises a protein containing the fusion molecule and a protein containing the regulatory factor separated at the cleavage sequence; and binding or dissociation between the regulatory factor and the marker protein promotes or reduces the degradation of the marker protein, and wherein the fusion protein comprises the components positioned from N-terminus to C-terminus in the following order:

(1) the fluorescent or luminescent protein, the marker protein, the cleavage sequence, and the regulatory factor;

(2) the marker protein, the fluorescent or luminescent protein, the cleavage sequence, and the regulatory factor;

(3) the regulatory factor, the cleavage sequence, the fluorescent or luminescent protein, and the marker protein; or (4) the regulatory factor, the cleavage sequence, the marker protein, and the fluorescent or luminescent protein.

* * * * *

```
                         SEQUENCE LISTING

<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggcctcgaga tgatggactt ggagctgccg                                       30

<210> SEQ ID NO 2
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aagctttggg ccaggattct cctcgacgtc accgcatgtt agaagacttc ctctgccctc      60
ggcagatcca ctggt                                                       75

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 3
ccgtaagctt atgcagccag atcccagg                                        28

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gctctagatt aacaggtaca gttctg                                          26

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggggaattcg ccaccatggt gagtgtgatt aaaccagag                             39

<210> SEQ ID NO 6
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atggatatcc gccctgggaa ggcaacattg agtaatgagc tactgcatct tctac          55

<210> SEQ ID NO 7
<211> LENGTH: 2940
<212> TYPE: DNA
<213> ORGANISM: Artificial Sequence
<220> FEATURE:
<223> OTHER INFORMATION: Description of Artificial Sequence: Synthetic
      DNA sequence of mKO2-Nrf2_100-T2A-Keap1

<400> SEQUENCE: 7
atggtgagtg tgattaaacc agagatgaag atgaggtact acatggacgg ctccgtcaat     60
gggcatgagt tcacaattga aggtgaaggc acaggcagac cttacgaggg acatcaagag    120
atgacactac gcgtcacaat ggccgagggc gggccaatgc ctttcgcgtt tgacttagtg    180
tcacacgtgt tctgttacgg ccacagagta tttactaaat atccagaaga gataccagac    240
tatttcaaac aagcatttcc tgaaggcctg tcatgggaaa ggtcgttgga gttcgaagat    300
ggtgggtccg cttcagtcag tgcgcatata agccttagag aaacaccttc taccacaaa    360 tccaaattta ctggggttaa cttttcctgcc gatggtccta tcatgcaaaa ccaaagtgtt    420
gattgggagc catcaaccga gaaaattact gccagcgacg gagttctgaa gggtgatgtt    480
acgatgtacc taaaacttga aggaggcggc aatcacaaat gccaaatgaa gactacttac    540
aaggcggcaa aagagattct tgaaatgcca ggagaccatt acatcggcca tcgcctcgtc    600
aggaaaaccg aaggcaacat tactgagcag gtagaagatg cagtagctca ttactcaatg    660
ttgccttccc agggcggata tccatcacac tggcggccgc tcgagatgat ggacttggag    720
ctgccgccgc cgggactccc gtcccagcag gacatggatt tgattgacat actttggagg    780
```

| | |
|---|---|
| caagatatag atcttggagt aagtcgagaa gtatttgact tcagtcagcg acggaaagag | 840 |
| tatgagctgg aaaaacagaa aaaacttgaa aaggaaagac aagaacaact ccaaaaggag | 900 |
| caagagaaag cctttttcgc tcagttacaa ctagatgaag agacaggtga atttctccca | 960 |
| attcagccag cccagcacat ccagtcagaa accagtggac ctgccgaggg cagaggaagt | 1020 |
| cttctaacat gcggtgacgt cgaggagaat cctggcccaa agcttatgca gccagatccc | 1080 |
| aggcctagcg gggctgggggc ctgctgccga ttcctgcccc tgcagtcaca gtgccctgag | 1140 |
| ggggcagggg acgcggtgat gtacgcctcc actgagtgca aggcggaggt gacgccctcc | 1200 |
| cagcatggca accgcacctt cagctacacc ctggaggatc ataccaagca ggcctttggc | 1260 |
| atcatgaacg agctgcggct cagccagcag ctgtgtgacg tcacactgca ggtcaagtac | 1320 |
| caggatgcac cggccgccca gttcatggcc cacaaggtgg tgctggcctc atccagccct | 1380 |
| gtcttcaagg ccatgttcac caacgggctg cgggagcagg catggaggt ggtgtccatt | 1440 |
| gagggtatcc accccaaggt catggagcgc ctcattgaat tcgcctacac ggcctccatc | 1500 |
| tccatgggcg agaagtgtgt cctccacgtc atgaacggtg ctgtcatgta ccagatcgac | 1560 |
| agcgttgtcc gtgcctgcag tgacttcctg gtgcagcagc tggaccccag caatgccatc | 1620 |
| ggcatcgcca acttcgctga gcagattggc tgtgtggagt gcaccagcg tgcccgggag | 1680 |
| tacatctaca tgcattttgg ggaggtggcc aagcaagagg agttcttcaa cctgtcccac | 1740 |
| tgccaactgg tgaccctcat cagccgggac gacctgaacg tgcgctgcga gtccgaggtc | 1800 |
| ttccacgcct gcatcaactg ggtcaagtac gactgcgaac agcgacggtt ctacgtccag | 1860 |
| gcgctgctgc gggccgtgcg ctgccactcg ttgacgccga acttcctgca gatgcagctg | 1920 |
| cagaagtgcg agatcctgca gtccgactcc cgctgcaagg actacctggt caagatcttc | 1980 |
| gaggagctca ccctgcacaa gcccacgcag gtgatgccct gccgggcgcc caaggtgggc | 2040 |
| cgcctgatct acaccgcggg cggctacttc gacagtcgc tcagctacct ggaggcttac | 2100 |
| aaccccagtg acggcacctg gctccggttg gcggacctgc aggtgccgcg gagcggcctg | 2160 |
| gccggctgcg tggtgggcgg gctgttgtac gccgtgggcg gcaggaacaa ctcgcccgac | 2220 |
| ggcaacaccg actccagcgc cctggactgt acaaccccca tgaccaatca gtggtcgccc | 2280 |
| tgcgccccca tgagcgtgcc ccgtaaccgc atcggggtgg gggtcatcga tggccacatc | 2340 |
| tatgccgtcg gcggctccca cggctgcatc caccacaaca gtgtggagag gtatgagcca | 2400 |
| gagcgggatg agtggcactt ggtggcccca atgctgacac gaaggatcgg ggtgggcgtg | 2460 |
| gctgtcctca atcgtctcct ttatgccgtg gggggctttg acgggacaaa ccgcccttaat | 2520 |
| tcagctgagt gttactaccc agagaggaac gagtggcgaa tgatcacagc aatgaacacc | 2580 |
| atccgaagcg gggcaggcgt ctgcgtcctg cacaactgta tctatgctgc tggggggctat | 2640 |
| gatggtcagg accagctgaa cagcgtggag cgctacgatg tggaaacaga gacgtggact | 2700 |
| ttcgtagccc ccatgaagca ccggcgaagt gccctgggga tcactgtcca ccaggggaga | 2760 |
| atctacgtcc ttggaggcta tgatggtcac acgttcctgg acagtgtgga gtgttacgac | 2820 |
| ccagatacag acacctggag cgaggtgacc cgaatgacat cggccggag tggggtgggc | 2880 |
| gtggctgtca ccatggagcc ctgccggaag cagattgacc agcagaactg tacctgttga | 2940 |

<210> SEQ ID NO 8
<211> LENGTH: 18
<212> TYPE: PRT
<213> ORGANISM: Thosea asigna virus

```
<400> SEQUENCE: 8

Glu Gly Arg Gly Ser Leu Leu Thr Cys Gly Asp Val Glu Glu Asn Pro
1               5                   10                  15

Gly Pro

<210> SEQ ID NO 9
<211> LENGTH: 19
<212> TYPE: PRT
<213> ORGANISM: Porcine teschovirus

<400> SEQUENCE: 9

Ala Thr Asn Phe Ser Leu Leu Lys Gln Ala Gly Asp Val Glu Glu Asn
1               5                   10                  15

Pro Gly Pro
```